(12) United States Patent
Sun et al.

(10) Patent No.: US 9,650,620 B2
(45) Date of Patent: May 16, 2017

US009650620B2

(54) POLYPEPTIDES HAVING GLUCOAMYLASE ACTIVITY AND POLYNUCLEOTIDES ENCODING SAME

(75) Inventors: Tianqi Sun, Bejing (CN); Ming Li, Bejing (CN)

(73) Assignee: NOVOZYMES A/S, Bagsvaerd (DK)

( * ) Notice: Subject to any disclaimer, the term of this patent is extended or adjusted under 35 U.S.C. 154(b) by 98 days.

(21) Appl. No.: 14/241,344

(22) PCT Filed: Aug. 24, 2012

(86) PCT No.: PCT/CN2012/080553
§ 371 (c)(1),
(2), (4) Date: Feb. 26, 2014

(87) PCT Pub. No.: WO2013/029496
PCT Pub. Date: Mar. 7, 2013

(65) Prior Publication Data
US 2014/0206035 A1  Jul. 24, 2014

Related U.S. Application Data

(60) Provisional application No. 61/534,948, filed on Sep. 15, 2011.

(30) Foreign Application Priority Data

Aug. 26, 2011  (WO) ................ PCT/CN2011/078999

(51) Int. Cl.
C12P 19/02 (2006.01)
C12N 9/34 (2006.01)
C12P 19/20 (2006.01)

(52) U.S. Cl.
CPC ............ *C12N 9/2428* (2013.01); *C12P 19/02* (2013.01); *C12P 19/20* (2013.01); *C12Y 302/01003* (2013.01); *Y02P 20/52* (2015.11)

(58) Field of Classification Search
None
See application file for complete search history.

(56) References Cited

U.S. PATENT DOCUMENTS 6,255,084 B1 *  7/2001  Nielsen ................ C12N 9/2428
                                                                  435/205
2011/0078829 A1  3/2011  Tang

FOREIGN PATENT DOCUMENTS

| NL | WO 2014202616 A2 * | 12/2014 | ............. C07K 14/37 |
| WO | 99/28448 A1 | 6/1999 | |
| WO | 2005/045018 A1 | 5/2005 | |
| WO | 2007/057018 A2 | 5/2007 | |
| WO | WO 2008080093 A2 * | 7/2008 | ........... C12N 9/2414 |

OTHER PUBLICATIONS

Nielsen et al, 2002, Protein Expression and Purification, 26:1-8.*
Marin-Navarro et al, 2011, Appl. Microbiol. Biotechnol., 89:1267-1273.*
Fourgoux-Nicol et al, 1999, Plant Molecular Biology 40 :857-872.*

* cited by examiner

*Primary Examiner* — Jason Deveau Rosen
(74) *Attorney, Agent, or Firm* — David Fazzolare

(57) ABSTRACT

Provided are isolated polypeptides having glucoamylase activity, catalytic domains, and polynucleotides encoding the polypeptides, catalytic domains. Also provided are nucleic acid constructs, vectors and host cells comprising the polynucleotides as well as methods of producing and using the polypeptides, catalytic domains.

18 Claims, No Drawings

SEQUENCE LISTING

```
<160> NUMBER OF SEQ ID NOS: 8

<210> SEQ ID NO 1
<211> LENGTH: 1766
<212> TYPE: DNA
<213> ORGANISM: Talaromyces emersonii

<400> SEQUENCE: 1
atgttggtca agtccttgtt gtctcaagtt gccctgctgg cagtctcctt gggtgcctcg     60
gcagagtcgt tggtggcaca agcttccggc ctggatgtct tcatttcgtc agaatcagag    120
atcgctctgc gtggcgtctt ggccaatatt ggccccgacg gaaaagcagt tccgggagca    180
gatgcgggca ttgtggttgc gagcccatcc acggcgaacc ctgactgtga gtagatccca    240
ctattgccat gccagatcca ggacgctaat ctaatcgtgc tgtctccttc aagactggta    300
cacctggacg agagatgctg ccttaacgtt caaatacttg attgaccggt ttgtcgacgg    360
cgattcgtcc ctgcagggtc taatccagga ttacatctcc gcccaagcaa agctgcagac    420
cgtccagaac ccatcgggag acctttcctc cggagccggt ctttcagagc ccaagtttta    480
catcaatgag acggcctttc tgggccagtg gggtcgtccc caacgcgatg ggccggcatt    540
gcgtgccacg gctctgatcg catatgccca gtggctgata gacaatggct actcggacgt    600
cgctctctcg cacgtctggc ccattgcgag caatgatctg gcatatgtgg cccagtactg    660
gaaccagacc ggctatgacc tctgggaaga ggtcgacggt tcgtcgttct tcaccatttc    720
catctctcac cgggccctcg tcgagggagc tgcgctggcg aagcgcctca accagaccat    780
cggcgactac agttcggtag cctcccagat cctgtgcttc cagcagtcct tctggacggg    840
gagctacatc gactcgaata tcaatctggt gcacgacgtc aaccggactg gcaaagacgc    900
caactccatt ctggcctcga tccacgtctt cgatccggag gccgcatgtg acgattcaac    960
attccagccc tgctcgtcaa aggcgctggc gaaccacaaa gctgtcgtgg actcgttcag   1020
```

-continued

```
aaacctctat tctgtcaacc atggcattaa aagggatcc gcagtggcga tcggacggta    1080
tgcggaggat atatactacg acgggaatcc atggtaagga gtttcgttta ctgtctttca    1140
aacatggttt ttatctactt cgatcaacct ggaacaacaa ccctgatcta tcgtctaggt    1200
acctgtgcac actagcagca gccgaacagc tctatgatgc cctctatcag tggcgaaaac    1260
agggctcgct gaccatcaca tctgtctcac tgaagttctt ccgcgacttt gactcatccg    1320
tcaagaccgg aacgtaccct tcttcctcca acacctactc ctcgctgacg aaggcgatca    1380
aggcctatgc agacggcttc gtcagcatcg tgcagaaata cacgccggac aacggggccc    1440
tctcagagca attctccaaa gtcaacggca gtcagacgtc cgccatcgac ctcacatggt    1500
cctacgccgc cttcttgacg gcggccagcc gtcgcaacgg caccatgggc ccgagttggg    1560
gtgcatcgca ggcgagcagc gtcccgtcct cgtgcgcaac gaccacgctg aaaggaacct    1620
acaaagctgc gacggtgacg tcctggccga ccgggttggt cagcaagaac aatagcggca    1680
gcagtgcctc ggggacagcc actggttccg cgtccgcctc ctccacgagt aaaagcgccg    1740
gtagccctgg cgcagcagga gcatag                                        1766
```

<210> SEQ ID NO 2
<211> LENGTH: 537
<212> TYPE: PRT
<213> ORGANISM: Talaromyces emersonii

<400> SEQUENCE: 2

```
Met Leu Val Lys Ser Leu Leu Ser Gln Val Ala Leu Leu Ala Val Ser
1               5                   10                  15

Leu Gly Ala Ser Ala Glu Ser Leu Val Ala Gln Ala Ser Gly Leu Asp
            20                  25                  30

Val Phe Ile Ser Ser Glu Ser Glu Ile Ala Leu Arg Gly Val Leu Ala
        35                  40                  45

Asn Ile Gly Pro Asp Gly Lys Ala Val Pro Gly Ala Asp Ala Gly Ile
    50                  55                  60

Val Val Ala Ser Pro Ser Thr Ala Asn Pro Asp Tyr Trp Tyr Thr Trp
65                  70                  75                  80

Thr Arg Asp Ala Ala Leu Thr Phe Lys Tyr Leu Ile Asp Arg Phe Val
                85                  90                  95

Asp Gly Asp Ser Ser Leu Gln Gly Leu Ile Gln Asp Tyr Ile Ser Ala
            100                 105                 110

Gln Ala Lys Leu Gln Thr Val Gln Asn Pro Ser Gly Asp Leu Ser Ser
        115                 120                 125

Gly Ala Gly Leu Ser Glu Pro Lys Phe Tyr Ile Asn Glu Thr Ala Phe
    130                 135                 140

Leu Gly Gln Trp Gly Arg Pro Gln Arg Asp Gly Pro Ala Leu Arg Ala
145                 150                 155                 160

Thr Ala Leu Ile Ala Tyr Ala Gln Trp Leu Ile Asp Asn Gly Tyr Ser
                165                 170                 175

Asp Val Ala Leu Ser His Val Trp Pro Ile Ala Ser Asn Asp Leu Ala
            180                 185                 190

Tyr Val Ala Gln Tyr Trp Asn Gln Thr Gly Tyr Asp Leu Trp Glu Glu
        195                 200                 205

Val Asp Gly Ser Ser Phe Phe Thr Ile Ser Ile Ser His Arg Ala Leu
    210                 215                 220

Val Glu Gly Ala Ala Leu Ala Lys Arg Leu Asn Gln Thr Ile Gly Asp
225                 230                 235                 240
```

Tyr Ser Ser Val Ala Ser Gln Ile Leu Cys Phe Gln Gln Ser Phe Trp
            245                 250                 255

Thr Gly Ser Tyr Ile Asp Ser Asn Ile Asn Leu Val His Asp Val Asn
        260                 265                 270

Arg Thr Gly Lys Asp Ala Asn Ser Ile Leu Ala Ser Ile His Val Phe
    275                 280                 285

Asp Pro Glu Ala Ala Cys Asp Asp Ser Thr Phe Gln Pro Cys Ser Ser
290                 295                 300

Lys Ala Leu Ala Asn His Lys Ala Val Val Asp Ser Phe Arg Asn Leu
305                 310                 315                 320

Tyr Ser Val Asn His Gly Ile Lys Lys Gly Ser Ala Val Ala Ile Gly
            325                 330                 335

Arg Tyr Ala Glu Asp Ile Tyr Tyr Asp Gly Asn Pro Trp Tyr Leu Cys
        340                 345                 350

Thr Leu Ala Ala Ala Glu Gln Leu Tyr Asp Ala Leu Tyr Gln Trp Arg
    355                 360                 365

Lys Gln Gly Ser Leu Thr Ile Thr Ser Val Ser Leu Lys Phe Phe Arg
370                 375                 380

Asp Phe Asp Ser Ser Val Lys Thr Gly Thr Tyr Pro Ser Ser Ser Asn
385                 390                 395                 400

Thr Tyr Ser Ser Leu Thr Lys Ala Ile Lys Ala Tyr Ala Asp Gly Phe
            405                 410                 415

Val Ser Ile Val Gln Lys Tyr Thr Pro Asp Asn Gly Ala Leu Ser Glu
        420                 425                 430

Gln Phe Ser Lys Val Asn Gly Ser Gln Thr Ser Ala Ile Asp Leu Thr
    435                 440                 445

Trp Ser Tyr Ala Ala Phe Leu Thr Ala Ala Ser Arg Arg Asn Gly Thr
450                 455                 460

Met Gly Pro Ser Trp Gly Ala Ser Gln Ala Ser Ser Val Pro Ser Ser
465                 470                 475                 480

Cys Ala Thr Thr Thr Leu Lys Gly Thr Tyr Lys Ala Ala Thr Val Thr
            485                 490                 495

Ser Trp Pro Thr Gly Leu Val Ser Lys Asn Asn Ser Gly Ser Ser Ala
        500                 505                 510

Ser Gly Thr Ala Thr Gly Ser Ala Ser Ala Ser Thr Ser Lys Ser
    515                 520                 525

Ala Gly Ser Pro Gly Ala Ala Gly Ala
        530                 535

<210> SEQ ID NO 3
<211> LENGTH: 2171
<212> TYPE: DNA
<213> ORGANISM: Talaromyces emersonii

<400> SEQUENCE: 3
atggcttctc ctctgtctta tgcgctgttc gcgctcgccc tcagcccggc gttggtcatg      60
gcagacgctc tgctgaaacc gcgcgcaacg gccagcctga acagctggct ggcgacagag     120
acgcagtatg cgctcgaggc catcctgaac aacatcggcc gtcgggtgc gtgggcacaa     180 tcagccagcc cgggcatcgt cgtggccagt cccagcacga gtgatccaga ttgttgtatc     240
ctccagtaag aactgctgaa agaacaggaa gctaaccttg tcgcaacgcc agactactac     300
acctggacgc gagactcggc gctgaccttc aaggtgctga tcgacctctt caagaacggc     360
aactccagcc tgcagggcgt gatcgaggag tacatcgatg cgcaggccta tatccagacg     420

-continued

```
gtgtccaatc catctggctc cctgtctacg ggtggtctgg gggagcccaa gttcaatgtc    480
aacagggccg catttactgg cagctggggt cgtccgcagc gagatgggcc ggctctacgc    540
gctactgcgc tgattgcttt tggcgaatgg ctgattgtga gtttccgtct tgaaaacaaa    600
tacttcagat ggctaacatg ccaaggataa tggctatacg acgtatgcgt ctgatattgt    660
gtggcccatt gtgcgcaatg atctgtcata cgttgcacag tattggaacg agactagttt    720
cggtaggttt ttctcttcca tcaccttggt acgaattctg cttattcgaa tgcaagatct    780
ctgggaggaa gtcgacgggt cttcgttctt taccatcgcc gtccagcatc gcgcgatggt    840
cgagggagcc aactttgcca gcgcactggg aacgtcatgc tcgtactgca cctctcaggc    900
tcccgagatc tctgctaccc tgcagtcctt ctggacgggg tcctacatcc tggccaactt    960
ccagagtagc cgctcaggaa aggacgtcaa caccatccta ggcagcatcc acacgtttga   1020
ccccgaggcg ggctgtgatg acaccacctt ccagccctgt tcgccaaggg cacttgcgaa   1080
tcacaaagtc gtggtggacg ccttccgaga cctctacgct atcaacaaca atgccgctgg   1140
aggtgtcgcc gtggccgtgg gccggtatcc cgaggacaca tactacaatg caacccgtg   1200 gttcctgtgc acgcttgctg cagccgagca gctgtacgat gctctgtatc agtggaacag   1260
cattggatcc atcaccatca ccgacgtctc tttgggtttc ttccaggact tgtataacga   1320
tgccgcagtg ggcacgcact cttcctcgag ctcagagtac agtgcgatcg tggatgcggt   1380
gaagacctac gccgacggat tcatgagcat cgtggtgcgt catcctttat ctctcgcaaa   1440
agaaacccta gctgatatcc ctctaggaaa actacgccct gacgaacgga tccctctccg   1500
agcaatactc caagacggac ggaacacagg agtccgctcg cgatctcacc tggtcgtacg   1560
ctgccttgct gacggccaac atgcgtcgca actccgtggt tcccgccgcc tggggcgaga   1620
cggctgccag cagtgtgccg gcgacctgtg tgtccacctc tgcgacaggc gtctacagca   1680
ctgctacaga tacagcctgg ccgagcacgt tgactgcagc tacaaccacg gcaacgacaa   1740
ccacaagcag ggccacgaca gcaagaccca caggcacagg aacaacatca acagcaacaa   1800
cctcatcctc atcatcatca tgtacgaccc ccacaaccat ggccataacc ttcaaactaa   1860
ccgcaacaac ctactacgga gaaaacatca agatgacagg ctcaatcccg cagctcggcg   1920
actggaaccc tgacgacgca gtggctttga gcgcagcgaa ctacacgagc actgacccgc   1980
tgtggttcgt cactatcaac ctgcctgcgg gcctgtcatt tgagtacaag tacatccgca   2040
tcgagagcga tgggacggtc gtgtgggaga gtgatccgaa tcggttgtat acggttcctt   2100
cttcggcttc agcatgtggt gagacggttg ctactgctgc tgctgttgtt gagagcgata   2160
cgtggcggtg a                                                       2171
```

<210> SEQ ID NO 4
<211> LENGTH: 651
<212> TYPE: PRT
<213> ORGANISM: Talaromyces emersonii

<400> SEQUENCE: 4

```
Met Ala Ser Pro Leu Ser Tyr Ala Leu Phe Ala Leu Ala Leu Ser Pro
1               5                   10                  15

Ala Leu Val Met Ala Asp Ala Leu Leu Lys Pro Arg Ala Thr Ala Ser
            20                  25                  30

Leu Asn Ser Trp Leu Ala Thr Glu Thr Gln Tyr Ala Leu Glu Ala Ile
        35                  40                  45

Leu Asn Asn Ile Gly Pro Ser Gly Ala Trp Ala Gln Ser Ala Ser Pro
    50                  55                  60
```

-continued

```
Gly Ile Val Val Ala Ser Pro Ser Thr Ser Asp Pro Asp Tyr Tyr Tyr
 65                  70                  75                  80

Thr Trp Thr Arg Asp Ser Ala Leu Thr Phe Lys Val Leu Ile Asp Leu
                 85                  90                  95

Phe Lys Asn Gly Asn Ser Ser Leu Gln Gly Val Ile Glu Glu Tyr Ile
            100                 105                 110

Asp Ala Gln Ala Tyr Ile Gln Thr Val Ser Asn Pro Ser Gly Ser Leu
        115                 120                 125

Ser Thr Gly Gly Leu Gly Glu Pro Lys Phe Asn Val Asn Arg Ala Ala
130                 135                 140

Phe Thr Gly Ser Trp Gly Arg Pro Gln Arg Asp Gly Pro Ala Leu Arg
145                 150                 155                 160

Ala Thr Ala Leu Ile Ala Phe Gly Glu Trp Leu Ile Asp Asn Gly Tyr
                165                 170                 175

Thr Thr Tyr Ala Ser Asp Ile Val Trp Pro Ile Val Arg Asn Asp Leu
            180                 185                 190

Ser Tyr Val Ala Gln Tyr Trp Asn Glu Thr Ser Phe Asp Leu Trp Glu
        195                 200                 205

Glu Val Asp Gly Ser Ser Phe Phe Thr Ile Ala Val Gln His Arg Ala
210                 215                 220

Met Val Glu Gly Ala Asn Phe Ala Ser Ala Leu Gly Thr Ser Cys Ser
225                 230                 235                 240

Tyr Cys Thr Ser Gln Ala Pro Glu Ile Leu Cys Tyr Leu Gln Ser Phe
                245                 250                 255

Trp Thr Gly Ser Tyr Ile Leu Ala Asn Phe Gln Ser Ser Arg Ser Gly
            260                 265                 270

Lys Asp Val Asn Thr Ile Leu Gly Ser Ile His Thr Phe Asp Pro Glu
        275                 280                 285

Ala Gly Cys Asp Asp Thr Thr Phe Gln Pro Cys Ser Pro Arg Ala Leu
290                 295                 300

Ala Asn His Lys Val Val Val Asp Ala Phe Arg Asp Leu Tyr Ala Ile
305                 310                 315                 320

Asn Asn Asn Ala Ala Gly Gly Val Ala Val Ala Val Gly Arg Tyr Pro
                325                 330                 335

Glu Asp Thr Tyr Tyr Asn Gly Asn Pro Trp Phe Leu Cys Thr Leu Ala
            340                 345                 350

Ala Ala Glu Gln Leu Tyr Asp Ala Leu Tyr Gln Trp Asn Ser Ile Gly
        355                 360                 365

Ser Ile Thr Ile Thr Asp Val Ser Leu Gly Phe Phe Gln Asp Leu Tyr
370                 375                 380

Asn Asp Ala Ala Val Gly Thr His Ser Ser Ser Ser Glu Tyr Ser
385                 390                 395                 400

Ala Ile Val Asp Ala Val Lys Thr Tyr Ala Asp Gly Phe Met Ser Ile
                405                 410                 415

Val Glu Asn Tyr Ala Leu Thr Asn Gly Ser Leu Ser Glu Gln Tyr Ser
            420                 425                 430

Lys Thr Asp Gly Thr Gln Glu Ser Ala Arg Asp Leu Thr Trp Ser Tyr
        435                 440                 445

Ala Ala Leu Leu Thr Ala Asn Met Arg Arg Asn Ser Val Val Pro Ala
        450                 455                 460

Ala Trp Gly Glu Thr Ala Ala Ser Ser Val Pro Ala Thr Cys Val Ser
465                 470                 475                 480
```

```
Thr Ser Ala Thr Gly Val Tyr Ser Thr Ala Thr Asp Thr Ala Trp Pro
                485                 490                 495

Ser Thr Leu Thr Ala Ala Thr Thr Ala Thr Thr Thr Ser Arg
        500                 505                 510

Ala Thr Thr Ser Lys Thr Thr Gly Thr Gly Thr Thr Ser Thr Ala Thr
        515                 520                 525

Thr Ser Ser Ser Ser Ser Cys Thr Thr Pro Thr Thr Met Ala Ile
    530                 535                 540

Thr Phe Lys Leu Thr Ala Thr Thr Tyr Tyr Gly Glu Asn Ile Lys Met
545                 550                 555                 560

Thr Gly Ser Ile Pro Gln Leu Gly Asp Trp Asn Pro Asp Asp Ala Val
                565                 570                 575

Ala Leu Ser Ala Ala Asn Tyr Thr Ser Thr Asp Pro Leu Trp Phe Val
                580                 585                 590

Thr Ile Asn Leu Pro Ala Gly Leu Ser Phe Glu Tyr Lys Tyr Ile Arg
                595                 600                 605

Ile Glu Ser Asp Gly Thr Val Val Trp Glu Ser Asp Pro Asn Arg Leu
            610                 615                 620

Tyr Thr Val Pro Ser Ser Ala Ser Ala Cys Gly Glu Thr Val Ala Thr
625                 630                 635                 640

Ala Ala Ala Val Val Glu Ser Asp Thr Trp Arg
                645                 650
```

<210> SEQ ID NO 5
<211> LENGTH: 45
<212> TYPE: DNA
<213> ORGANISM: Artificial
<220> FEATURE:
<223> OTHER INFORMATION: PCR primer

<400> SEQUENCE: 5
acacaactgg ggatccaccc atgttggtca agtccttgtt gtctc            45

<210> SEQ ID NO 6
<211> LENGTH: 43
<212> TYPE: DNA
<213> ORGANISM: Artificial
<220> FEATURE:
<223> OTHER INFORMATION: PCR primer

<400> SEQUENCE: 6
ccctctagat ctcgagctat gctcctgctg cgccagggct acc              43

<210> SEQ ID NO 7
<211> LENGTH: 43
<212> TYPE: DNA
<213> ORGANISM: Artificial
<220> FEATURE:
<223> OTHER INFORMATION: PCR primer

<400> SEQUENCE: 7
acacaactgg ggatccacca tggcttctcc tctgtcttat gcg              43

<210> SEQ ID NO 8
<211> LENGTH: 36
<212> TYPE: DNA
<213> ORGANISM: Artificial
<220> FEATURE:
<223> OTHER INFORMATION: PCR primer

```
<400> SEQUENCE: 8
ccctctagat ctcgagtttc accgccacgt atcgct                                    36
```

POLYPEPTIDES HAVING GLUCOAMYLASE ACTIVITY AND POLYNUCLEOTIDES ENCODING SAME

CROSS-REFERENCE TO RELATED APPLICATIONS

This application is a 35 U.S.C. 371 national application of PCT/CN2012/080553 filed Aug. 24, 2012, which claims priority or the benefit under 35 U.S.C. 119 of International application no. PCT/CN11/078999 filed Aug. 26, 2011 and U.S. provisional application No. 61/534,948 filed Sep. 15, 2011, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to polypeptides having glucoamylase activity and polynucleotides encoding the polypeptides. The invention also relates to nucleic acid constructs, vectors, and host cells comprising the polynucleotides as well as methods for producing and using the polypeptides, and to the use of glucoamylases of the invention for starch conversion to producing fermentation products, such as ethanol, and syrups, such as glucose. The invention also relates to a composition comprising a glucoamylase of the invention.

Description of the Related Art

Glucoamylase (1,4-alpha-D-glucan glucohydrolase, EC 3.2.1.3) is an enzyme, which catalyzes the release of D-glucose from the non-reducing ends of starch or related oligo- and polysaccharide molecules. Glucoamylases are produced by several filamentous fungi and yeast, with those from *Aspergillus* being commercially most important.

Commercially, glucoamylases are used to convert starchy material, which is already partially hydrolyzed by an alpha-amylase, to glucose. The glucose may then be converted directly or indirectly into a fermentation product using a fermenting organism. Examples of commercial fermentation products include alcohols (e.g., ethanol, methanol, butanol, 1,3-propanediol); organic acids (e.g., citric acid, acetic acid, itaconic acid, lactic acid, gluconic acid, gluconate, lactic acid, succinic acid, 2,5-diketo-D-gluconic acid); ketones (e.g., acetone); amino acids (e.g., glutamic acid); gases (e.g., $H_2$ and $CO_2$), and more complex compounds, including, for example, antibiotics (e.g., penicillin and tetracycline); enzymes; vitamins (e.g., riboflavin, $B_{12}$, beta-carotene); hormones, and other compounds which are difficult to produce synthetically. Fermentation processes are also commonly used in the consumable alcohol (e.g., beer and wine), dairy (e.g., in the production of yogurt and cheese) industries.

The end product may also be syrup. For instance, the end product may be glucose, but may also be converted, e.g., by glucose isomerase to fructose or a mixture composed almost equally of glucose and fructose. This mixture, or a mixture further enriched with fructose, is the most commonly used high fructose corn syrup (HFCS) commercialized throughout the world. It is an object of the present invention to provide polypeptides having glucoamylase activity and polynucleotides encoding the polypeptides and which provide a high yield in fermentation product production processes, such as ethanol production processes, including one-step ethanol fermentation processes from un-gelatinized raw (or uncooked) starch. One of the glucoamylases according to the invention, SEQ ID NO: 2, shares 62.3% identity to GENESEQP:ASP18034 from *Phoma herbarum* included in WO2008080093-A2. Another glucoamylase of the invention, SEQ ID NO: 4, shares 73.0% identity to *GENESEQP: ASP*18042 from *Elaphocordyceps ophioglossoide* included in WO2008080093-A2.

SUMMARY OF THE INVENTION

Polypeptides produced by the fungus *Talaromyces* and having glucoamylase activity have been identified and characterized. More particularly the *Talaromyces* sp. is selected from *Talaromyces emersonii*.

The present invention relates to isolated polypeptides having glucoamylase activity, selected from the group consisting of:

(a) a polypeptide having at least 75%, at least 80%, at least 85%, at least 90%, e.g. at least 91%, at least 92%, at least 93%, at least 94%, at least 95%, at least 96%, at least 97%, at least 98%, at least 99%, or 100% sequence identity to the mature polypeptide of SEQ ID NO: 2 or SEQ ID NO: 4;

(b) a polypeptide encoded by a polynucleotide that hybridizes under medium-high stringency conditions, high stringency conditions, or very high stringency conditions with (i) the mature polypeptide coding sequence of SEQ ID NO: 1 or SEQ ID NO: 3, (ii) the cDNA sequence thereof, or (iii) the full-length complement of (i) or (ii);

(c) a polypeptide encoded by a polynucleotide having at least 75%, at least 80%, at least 85%, at least 90%, e.g. at least 91%, at least 92%, at least 93%, at least 94%, at least 95%, at least 96%, at least 97%, at least 98%, at least 99%, or 100% sequence identity to the mature polypeptide coding sequence of SEQ ID NO: 1 or SEQ ID NO: 3, or the cDNA sequence thereof;

(d) a variant of the mature polypeptide of SEQ ID NO: 2 or SEQ ID NO: 4 comprising a substitution, deletion, and/or insertion at one or more (several) positions; and (e) a fragment of the polypeptides of (a), (b), (c), or (d) that has glucoamylase activity.

The present invention also relates to isolated polypeptides comprising a glucoamylase catalytic domain selected from the group consisting of:

(a) a catalytic domain having at least 75% sequence identity to amino acids 31 to 500 of SEQ ID NO: 2 or amino acids 29 to 499 of SEQ ID NO: 4;

(b) a catalytic domain encoded by a polynucleotide that hybridizes under high stringency conditions with (i) nucleotides 91 to 1652 of SEQ ID NO: 1 or nucleotides 85 to 1712 of SEQ ID NO: 3, (ii) the cDNA sequences thereof, or (iii) the full-length complement of (i) or (ii);

(c) a catalytic domain encoded by a polynucleotide having at least 90% sequence identity to (i) nucleotides 91 to 1652 of SEQ ID NO: 1 or nucleotides 85 to 1712 of SEQ ID NO: 3, or (ii) or the cDNA sequence thereof; and (d) a variant of amino acids 31 to 500 of SEQ ID NO: 2 or amino acids 29 to 499 of SEQ ID NO: 4 comprising a substitution, deletion, and/or insertion at one or more (e.g., several) positions; and wherein the catalytic domain has glucoamylase activity.

The present invention also relates to isolated polynucleotides encoding the polypeptides of the present invention; nucleic acid constructs; recombinant expression vectors;

recombinant host cells comprising the polynucleotides; and methods of producing the polypeptides.

The present invention also relates to methods of producing a fermentation product from starch containing material and to compositions comprising the glucoamylase of the invention.

DEFINITIONS

Glucoamylase: The term glucoamylase (1,4-alpha-D-glucan glucohydrolase, EC 3.2.1.3) is defined as an enzyme, which catalyzes the release of D-glucose from the non-reducing ends of starch or related oligo- and polysaccharide molecules. For purposes of the present invention, glucoamylase activity is determined according to the procedure described in the 'Materials & Methods'-section herein.

The polypeptides of the present invention have at least 20%, preferably at least 40%, preferably at least 45%, more preferably at least 50%, more preferably at least 55%, more preferably at least 60%, more preferably at least 65%, more preferably at least 70%, more preferably at least 75%, more preferably at least 80%, more preferably at least 85%, even more preferably at least 90%, most preferably at least 95%, and even most preferably at least 100% of the glucoamylase activity of the mature polypeptide of SEQ ID NO: 2. or the polypeptides of the present invention have at least 20%, preferably at least 40%, preferably at least 45%, more preferably at least 50%, more preferably at least 55%, more preferably at least 60%, more preferably at least 65%, more preferably at least 70%, more preferably at least 75%, more preferably at least 80%, more preferably at least 85%, even more preferably at least 90%, most preferably at least 95%, and even most preferably at least 100% of the glucoamylase activity of the mature polypeptide of SEQ ID NO: 4.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Binding domain: The term "carbohydrate binding domain" means the region of an enzyme that mediates binding of the enzyme to the carbohydrate substrate. The carbohydrate binding domain (CBD) is typically found either at the N-terminal or at the C-terminal extremity of an glucoamylase. The CBD is also sometimes referred to as a starch binding domain, SBD.

Catalytic domain: The term "catalytic domain" means the region of an enzyme containing the catalytic machinery of the enzyme.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fragment: The term "fragment" means a polypeptide or a catalytic or carbohydrate binding domain having one or more (e.g., several) amino acids absent from the amino and/or carboxyl terminus of a mature polypeptide or domain; wherein the fragment has glucoamylase or carbohydrate binding activity. In one aspect, a fragment contains at least 85% amino acid residues, at least 90% amino acid residues, or at least 95% amino acid residues of SEQ ID NO: 2 or SEQ ID NO: 4. In one specific embodiment a fragment comprises amino acids 31 to 500 of SEQ ID NO: 2 or amino acids 29 to 499 of SEQ ID NO: 4.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 22 to 537 of SEQ ID NO: 2 based on the SignalP program (Nielsen et al., 1997, *Protein Engineering* 10:1-6) that predicts amino acids 1 to 21 of SEQ ID NO: 2 are a signal peptide. In another aspect, the mature polypeptide is amino acids 22 to 651 of SEQ ID NO: 4 based on the SignalP program (Nielsen et al, 1997, *Protein Engineering* 10:1-6) that predicts amino acids 1 to 21 of SEQ ID NO: 4 are a signal peptide.

It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having glucoamylase activity. In one aspect, the mature polypeptide coding sequence is nucleotides 64 to 1763 of SEQ ID NO: 1 or the cDNA sequence thereof based on the SignalP (Nielsen et al., 1997, supra) that predicts nucleotides 1 to 63 of SEQ ID NO: 1 encode a signal peptide. In another aspect the mature polypeptide coding sequence is nucleotides 64-226, 294-1113, and 1199-1763 of SEQ ID NO 1.

In another aspect, the mature polypeptide coding sequence is nucleotides 64 to 2168 of SEQ ID NO: 3 or the cDNA sequence thereof based on the SignalP (Nielsen et al, 1997, supra) that predicts nucleotides 1 to 63 of SEQ ID NO: 3 encode a signal peptide. In another aspect the mature polypeptide coding sequence is nucleotides 64-232, 293-576, 626-722, 777-1414, and 1467-2168 of SEQ ID NO 3.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and either 35% formamide, following standard Southern blotting procedures for 12 to 24 hours. The carrier material is finally washed three times each for 15 minutes using 2×SSC, 0.2% SDS at 60° C.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Sequence identity: The relatedness between two amino acid sequences or between two nucleotide sequences is described by the parameter "sequence identity". For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of
Alignment−Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having glucoamylase activity. In one aspect, a subsequence contains at least 85% nucleotides, at least 90% nucleotides, or at least 95% nucleotides of SEQ ID NO: 1 or SEQ ID NO: 3. In a particular embodiment a subsequence comprises nucleotides 91 to 1652 of SEQ ID NO: 1, or nucleotides 85 to 1712 of SEQ ID NO: 3.

Variant: The term "variant" means a polypeptide having glucoamylase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

DETAILED DESCRIPTION OF THE INVENTION

Polypeptides Having Glucoamylase Activity

In an embodiment, the present invention relates to isolated polypeptides having a sequence identity to the mature polypeptide of SEQ ID NO: 2 of at least 75%, at least 80%, at least 85%, at least 86%, e.g. at least 87%, at least 88%, at least 89%, at least 90%, at least 91%, at least 92%, at least 93%, at least 94%, at least 95%, at least 96%, at least 97%, at least 98%, at least 99%, or 100%, which have glucoamylase activity. In particular the glucoamylase have at least 20%, preferably at least 40%, preferably at least 45%, more preferably at least 50%, more preferably at least 55%, more preferably at least 60%, more preferably at least 65%, more preferably at least 70%, more preferably at least 75%, more preferably at least 80%, more preferably at least 85%, even more preferably at least 90%, most preferably at least 95%, and even most preferably at least 100% of the glucoamylase activity of the mature polypeptide of SEQ ID NO: 2.

In one aspect, the polypeptides differ by no more than 10 amino acids, e.g., 1, 2, 3, 4, 5, 6, 7, 8, or 9, from the mature polypeptide of SEQ ID NO: 2.

A polypeptide of the present invention preferably comprises or consists of the amino acid sequence of SEQ ID NO: 2 or an allelic variant thereof; or is a fragment thereof having glucoamylase activity. In another aspect, the polypeptide comprises or consists of the mature polypeptide of SEQ ID NO: 2. In another aspect, the polypeptide comprises or consists of amino acids 64 to 537 of SEQ ID NO: 2.

In another embodiment, the present invention relates to isolated polypeptides having a sequence identity to the mature polypeptide of SEQ ID NO: 4 of at least 75%, at least 80%, at least 85% at least 86%, e.g. at least 87%, at least 88%, at least 89%, at least 90%, at least 91%, at least 92%, at least 93%, at least 94%, at least 95%, at least 96%, at least 97%, at least 98%, at least 99%, or 100%, which have glucoamylase activity. In particular the glucoamylase have at least 20%, preferably at least 40%, preferably at least 45%, more preferably at least 50%, more preferably at least 55%, more preferably at least 60%, more preferably at least 65%, more preferably at least 70%, more preferably at least 75%, more preferably at least 80%, more preferably at least 85%, even more preferably at least 90%, most preferably at least 95%, and even most preferably at least 100% of the glucoamylase activity of the mature polypeptide of SEQ ID NO: 4. In one aspect, the polypeptides differ by no more than 10 amino acids, e.g., 1, 2, 3, 4, 5, 6, 7, 8, or 9, from the mature polypeptide of SEQ ID NO: 4.

A polypeptide of the present invention preferably comprises or consists of the amino acid sequence of SEQ ID NO: 4 or an allelic variant thereof; or is a fragment thereof having glucoamylase activity. In another aspect, the polypeptide comprises or consists of the mature polypeptide of SEQ ID NO: 4. In another aspect, the polypeptide comprises or consists of amino acids 64 to 545 of SEQ ID NO: 4.

In another embodiment, the present invention relates to an isolated polypeptide having glucoamylase activity encoded by a polynucleotide that hybridizes under medium-high stringency conditions, high stringency conditions, or very high stringency conditions with (i) the mature polypeptide coding sequence of SEQ ID NO: 1, (ii) the cDNA sequence thereof, or (iii) the full-length complement of (i) or (ii) (Sambrook et al., 1989, *Molecular Cloning, A Laboratory Manual*, 2d edition, Cold Spring Harbor, N.Y.).

In another embodiment, the present invention relates to an isolated polypeptide having glucoamylase activity encoded by a polynucleotide that hybridizes under medium-high stringency conditions, high stringency conditions, or very high stringency conditions with (i) the mature polypeptide coding sequence of SEQ ID NO: 3, (ii) the cDNA sequence thereof, or (iii) the full-length complement of (i) or (ii) (Sambrook et al., 1989, *Molecular Cloning, A Laboratory Manual*, 2d edition, Cold Spring Harbor, N.Y.).

The polynucleotide of SEQ ID NO: 1 or SEQ ID NO: 3, or a subsequence thereof, as well as the polypeptide of SEQ ID NO: 2 or SEQ ID NO: 4, or a fragment thereof, may be used to design nucleic acid probes to identify and clone DNA encoding polypeptides having glucoamylase activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having glucoamylase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1 or a subsequence thereof, the carrier material is used in a Southern blot.

For purposes of the present invention, hybridization indicates that the polynucleotide hybridizes to a labeled nucleic acid probe corresponding to (i) SEQ ID NO: 1 or SEQ ID NO: 3; (ii) the mature polypeptide coding sequence of SEQ ID NO: 1 or SEQ ID NO: 3; (iii) the cDNA sequences thereof; (iv) the full-length complement thereof; or (v) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is nucleotides 64-226, 294-1113, and 1199-1763 of SEQ ID NO 1. In another aspect, the nucleic acid probe is a polynucleotide that encodes the polypeptide of SEQ ID NO: 2; the mature polypeptide thereof; or a fragment thereof. In another aspect, the nucleic acid probe is SEQ ID NO: 1 or the cDNA sequence thereof.

In one aspect, the nucleic acid probe is nucleotides 64-232, 293-576, 626-722, 777-1414, and 1467-2168 of SEQ ID NO 3. In another aspect, the nucleic acid probe is a polynucleotide that encodes the polypeptide of SEQ ID NO: 4; the mature polypeptide thereof; or a fragment thereof. In another aspect, the nucleic acid probe is SEQ ID NO: 3 or the cDNA sequence thereof.

In another embodiment, the present invention relates to an isolated polypeptide having glucoamylase activity encoded by a polynucleotide having a sequence identity to the mature polypeptide coding sequence of SEQ ID NO: 1 or the cDNA sequence thereof of at least 75%, at least 80%, at least 85% at least 86%, e.g. at least 87%, at least 88%, at least 89%, at least 90%, at least 91%, at least 92%, at least 93%, at least 94%, at least 95%, at least 96%, at least 97%, at least 98%, at least 99%, or 100%.

In another embodiment, the present invention relates to an isolated polypeptide having glucoamylase activity encoded by a polynucleotide having a sequence identity to the mature polypeptide coding sequence of SEQ ID NO: 3 or the cDNA sequence thereof of at least 75%, at least 80%, at least 85% at least 86%, at least 87%, at least 88%, at least 89%, at least 90%, at least 91%, at least 92%, at least 93%, at least 94%, at least 95%, at least 96%, at least 97%, at least 98%, at least 99%, or 100%.

In another embodiment, the present invention relates to variants of the mature polypeptide of SEQ ID NO: 2 or SEQ ID NO: 4 comprising a substitution, deletion, and/or insertion at one or more (e.g., several) positions. In an embodiment, the number of amino acid substitutions, deletions and/or insertions introduced into the mature polypeptide of SEQ ID NO: 2 or SEQ ID NO: 4 is not more than 10, e.g., 1, 2, 3, 4, 5, 6, 7, 8 or 9. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for glucoamylase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al, 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al, 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al, 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Sources of Polypeptides Having Glucoamylase Activity

A polypeptide having glucoamylase activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a fungal polypeptide. For example, the polypeptide may be a *Penicillium* or a *Talaromyces* polypeptide.

In another aspect, the polypeptide is a *Penicillium emersonii* or a *Talaromyces emersonii* polypeptide.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Catalytic Domains

In one embodiment, the present invention also relates to catalytic domains having a sequence identity to amino acids 31 to 500 of SEQ ID NO: 2 of at least 75%, at least 80%, at least 85% at least 86%, e.g. at least 87%, at least 88%, at least 89%, at least 90%, at least 95%, at least 96%, at least 97%, at least 98%, at least 99%, or 100%. In one aspect, the catalytic domains comprise amino acid sequences that differ by no more than 10 amino acids, e.g., 1, 2, 3, 4, 5, 6, 7, 8, or 9, from amino acids 31 to 500 of SEQ ID NO: 2.

The catalytic domain preferably comprises or consists of amino acids 31 to 500 of SEQ ID NO: 2 or an allelic variant thereof; or is a fragment thereof having glucoamylase activity.

In another embodiment, the present invention also relates to catalytic domains encoded by polynucleotides that hybridize under high stringency conditions, or very high stringency conditions (as defined above) with (i) the nucleotides 91 to 1652 of SEQ ID NO: 1, (ii) the cDNA sequence thereof, or (iii) the full-length complement of (i) or (ii) (Sambrook et al., 1989, supra).

In another embodiment, the present invention also relates to catalytic domains encoded by polynucleotides having a sequence identity to nucleotides 91 to 1652 of SEQ ID NO: 1 or the cDNA sequence thereof of at least 75%, at least 80%, at least 85% at least 86%, e.g. at least 87%, at least 88%, at least 89%, at least 90%, at least 95%, at least 96%, at least 97%, at least 98%, at least 99%, or 100%.

In another embodiment, the present invention also relates to catalytic domain variants of amino acids 31 to 500 of SEQ ID NO: 2 comprising a substitution, deletion, and/or insertion at one or more (e.g., several) positions. In one aspect, the number of amino acid substitutions, deletions and/or insertions introduced into the sequence of amino acids 31 to 500 of SEQ ID NO: 2 is 10, e.g., 1, 2, 3, 4, 5, 6, 8, or 9.

In another embodiment, the present invention also relates to catalytic domains having a sequence identity to amino acids 29 to 499 of SEQ ID NO: 4 of at least 75%, at least 80%, at least 85% at least 86%, e.g. at least 87%, at least 88%, at least 89%, at least 90%, at least 95%, at least 96%, at least 97%, at least 98%, at least 99%, or 100%. In one aspect, the catalytic domains comprise amino acid sequences that differ by no more than 10 amino acids, e.g., 1, 2, 3, 4, 5, 6, 7, 8, or 9, from amino acids 29 to 499 of SEQ ID NO: 4.

The catalytic domain preferably comprises or consists of amino acids 29 to 499 of SEQ ID NO: 4 or an allelic variant thereof; or is a fragment thereof having glucoamylase activity.

In another embodiment, the present invention also relates to catalytic domains encoded by polynucleotides that hybridize under high stringency conditions, or very high stringency conditions (as defined above) with (i) the nucleotides 85 to 1712 of SEQ ID NO: 3, (ii) the cDNA sequence thereof, or (iii) the full-length complement of (i) or (ii) (Sambrook et al., 1989, supra).

In another embodiment, the present invention also relates to catalytic domains encoded by polynucleotides having a sequence identity to nucleotides 85 to 1712 of SEQ ID NO: 3 or the cDNA sequence thereof of at least 75%, at least 80%, at least 85% at least 86%, e.g. at least 87%, at least 88%, at least 89%, at least 90%, at least 95%, at least 96%, at least 97%, at least 98%, at least 99%, or 100%.

In another embodiment, the present invention also relates to catalytic domain variants of amino acids 29 to 499 of SEQ ID NO: 4 comprising a substitution, deletion, and/or insertion at one or more (e.g., several) positions. In one aspect, the number of amino acid substitutions, deletions and/or insertions introduced into the sequence of amino acids 29 to 499 of SEQ ID NO: 4 is 10, e.g., 1, 2, 3, 4, 5, 6, 8, or 9.

Binding Domains

In one embodiment, the present invention also relates to carbohydrate binding domains having a sequence identity to amino acids 536 to 651 of SEQ ID NO: 4 of at least 90%, at least 91%, at least 92%, at least 93%, at least 94%, at least 95%, at least 96%, at least 97%, at least 98%, at least 99%, or 100%. In one aspect, the carbohydrate binding domain comprise amino acid sequences that differ by no more than 10 amino acids, e.g., 1, 2, 3, 4, 5, 6, 7, 8, or 9, from amino acids 536 to 651 of SEQ ID NO: 4.

The carbohydrate binding domain preferably comprises or consists of amino acids 536 to 651 of SEQ ID NO: 4 or an allelic variant thereof; or is a fragment thereof having carbohydrate binding activity.

In another embodiment, the present invention also relates to carbohydrate binding domain variants of amino acids 536 to 651 of SEQ ID NO: 4 comprising a substitution, deletion, and/or insertion at one or more (e.g., several) positions. In one aspect, the number of amino acid substitutions, deletions and/or insertions introduced into the sequence of amino acids 536 to 651 of SEQ ID NO: 4 is 10, e.g., 1, 2, 3, 4, 5, 6, 8, or 9.

A catalytic domain operably linked to the carbohydrate binding domain may be from a hydrolase, isomerase, ligase, lyase, oxidoreductase, or transferase, e.g., an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase, xylanase, or beta-xylosidase. The polynucleotide encoding the catalytic domain may be obtained from any prokaryotic, eukaryotic, or other source.

In one particular embodiment the catalytic domain is the catalytic domain of the invention comprised in SEQ ID NO: 2 or SEQ ID NO: 4.

Hybrid Enzymes

The present invention also relates to hybrid enzymes comprising a catalytic domain having enzyme activity (e.g., starch degrading enzyme activity, such as alpha-amylase, amylopullulanase, beta-amylase, CGTase, glucoamylase, isoamylase, maltogenic amylase, or pullulanase activity), and a carbohydrate-binding domain (CBD). The hybrid enzyme may further comprise a linker.

The hybrid may be produced by fusing a first DNA sequence encoding a catalytic domain and a second DNA sequence encoding a carbohydrate-binding module, or the hybrid may be produced as a completely synthetic gene based on knowledge of the amino acid sequences of suitable CBDs, linkers and catalytic domains.

The term "hybrid enzyme" (also referred to as "fusion protein", "hybrid", hybrid polypeptide" or "hybrid protein") is used herein to characterize the hybrid polypeptides of the invention comprising a catalytic module having enzyme activity (e.g., starch degrading enzyme activity, such as alpha-amylase, amylopullulanase, beta-amylase, CGTase, glucoamylase, isoamylase, maltogenic amylase, or pullulanase activity) and a carbohydrate-binding module wherein the catalytic domain and the carbohydrate-binding module are derived from different sources. The term "source" includes, but is not limited to, a parent enzyme or a variant thereof, e.g., an amylase or glucoamylase, or other catalytic activity comprising a suitable catalytic module and/or a suitable CBD and/or a suitable linker. However the CBD may also be derived from a polypeptide having no catalytic activity. The catalytic domain and the carbohydrate binding module may be derived from the same microbial strain, from strains within the same species, from closely related species or less related organisms. Preferably the catalytic domain and the carbohydrate binding module of the hybrids are derived from different sources, e.g., from different enzymes from the same strain and/or species, or e.g., from strains within different species.

In one aspect the hybrid enzyme comprises the CBD according to the invention and a catalytic domain. The catalytic domain is in a particular embodiment a glucoamylase catalytic domain or an alpha-amylase catalytic domain. In another aspect the hybrid enzyme comprises a catalytic domain of the invention and a glycoamylase CBD or an alpha amylase CBD. Examples of suitable CBDs and linkers may be found e.g. in WO06/069290.

Polynucleotides

The present invention also relates to isolated polynucleotides encoding a polypeptide, a catalytic domain, or carbohydrate binding domain of the present invention, as described herein.

The techniques used to isolate or clone a polynucleotide are known in the art and include isolation from genomic DNA or cDNA, or a combination thereof. The cloning of the polynucleotides from genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Talaromyces*, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO: 1 or SEQ ID NO: 3, or the cDNA sequences thereof, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dania (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al, 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular. Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase,

*Bacillus stearothermophilus* neutral proteases (nprT, nprS, nprM), and *Bacillus subtilis prsA*. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al, 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, Soc. App. Bacteriol. Symposium Series No. 9, 1980).

The yeast host cell may be a *Candida, Hansenula, Kluyveromyces, Pichia, Saccharomyces, Schizosaccharomyces*, or *Yarrowia* cell, such as a *Kluyveromyces lactis, Saccharomyces carlsbergensis, Saccharomyces cerevisiae*,

*Saccharomyces diastaticus, Saccharomyces douglasii, Saccharomyces kluyveri, Saccharomyces norbensis, Saccharomyces oviformis,* or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiaturn, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al, 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and (b) recovering the polypeptide. In a preferred aspect, the cell is a *Penicillium* or a *Talaromyces* cell. In a more preferred aspect, the cell is a *Penicillium emersonii* or a *Talaromyces emersonii* cell. The present invention also relates to methods of producing a polypeptide of the present invention, comprising (a) cultivating a recombinant host cell of the present invention under conditions conducive for production of the polypeptide; and (b) recovering the polypeptide.

The host cells are cultivated in a nutrient medium suitable for production of the polypeptide using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Plants

The present invention also relates to isolated plants, e.g., a transgenic plant, plant part, or plant cell, comprising a polynucleotide of the present invention so as to express and produce a polypeptide or domain in recoverable quantities. The polypeptide or domain may be recovered from the plant or plant part. Alternatively, the plant or plant part containing the polypeptide or domain may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing the polypeptide or domain may be constructed in accordance with methods known in the art. In short, the plant or plant cell is constructed by incorporating one or more expression constructs encoding the polypeptide or domain into the plant host genome or chloroplast genome and propagating the resulting modified plant or plant cell into a transgenic plant or plant cell.

The expression construct is conveniently a nucleic acid construct that comprises a polynucleotide encoding a polypeptide or domain operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide or domain is desired to be expressed. For instance, the expression of the gene encoding a polypeptide or domain may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al, 1980, *Cell* 21: 285-294; Christensen et al, 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al, 1993, *Plant Physiol.* 102: 991-1000), the *chlorella* virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide or domain in the plant. For instance, the promoter enhancer element may be an intron that is placed between the promoter and the polynucleotide encoding a polypeptide or domain. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al, 1992, *Bio/Technology* 10: 667-674). An alternative method for transformation of monocots is based on protoplast transformation as described by Omirulleh et al., 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a polypeptide or domain can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a polypeptide or domain of the present invention comprising (a) cultivating a transgenic plant or a plant cell comprising a polynucleotide encoding the polypeptide or domain under conditions conducive for production of the polypeptide or domain; and (b) recovering the polypeptide or domain.

Compositions

The present invention also relates to compositions comprising a polypeptide of the present invention. Preferably, the compositions are enriched in such a polypeptide. The term "enriched" indicates that the glucoamylase activity of the composition has been increased, e.g., with an enrichment factor of at least 1.1.

The composition may comprise a polypeptide of the present invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by a microorganism belonging to the genus *Aspergillus*, preferably *Aspergillus aculeatus, Aspergillus awamori, Aspergillus fumigatus, Aspergillus foetidus, Aspergillus japonicus, Aspergillus nidulans, Aspergillus niger,* or *Aspergillus oryzae; Fusarium,* preferably *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sulphureum, Fusarium toruloseum, Fusarium trichothecioides,* or *Fusarium venenatum; Humicola,* preferably *Humicola insolens* or *Humicola lanuginosa;* or *Trichoderma,* preferably *Trichoderma harzianum, Trichoderma koningii, Trichoderma longibrachiatum, Trichoderma reesei,* or *Trichoderma viride.*

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Combination of Glucoamylase and Acid Alpha-Amylase

According to this aspect of the invention a glucoamylase of the invention may be combined with an alpha-amylase, preferably acid alpha-amylase in a ratio of between 0.3 and 5.0 AFAU/AGU. More preferably the ratio between acid alpha-amylase activity and glucoamylase activity is at least 0.35, at least 0.40, at least 0.50, at least 0.60, at least 0.7, at least 0.8, at least 0.9, at least 1.0, at least 1.1, at least 1.2, at least 1.3, at least 1.4, at least 1.5, at least 1.6, at least 1.7, at least 1.8, at least 1.85, or even at least 1.9 AFAU/AGU. However, the ratio between acid alpha-amylase activity and glucoamylase activity should preferably be less than 4.5, less than 4.0, less than 3.5, less than 3.0, less than 2.5, or even less than 2.25 AFAU/AGU. In AUU/AGI the activities of acid alpha-amylase and glucoamylase are preferably present in a ratio of between 0.4 and 6.5 AUU/AGI. More preferably the ratio between acid alpha-amylase activity and glucoamylase activity is at least 0.45, at least 0.50, at least 0.60, at least 0.7, at least 0.8, at least 0.9, at least 1.0, at least 1.1, at least 1.2, at least 1.3, at least 1.4, at least 1.5, at least 1.6, at least 1.7, at least 1.8, at least 1.9, at least 2.0, at least 2.1, at least 2.2, at least 2.3, at least 2.4, or even at least 2.5 AUU/AGI. However, the ratio between acid alpha-amylase activity and glucoamylase activity is preferably less than 6.0, less than 5.5, less than 4.5, less than 4.0, less than 3.5, or even less than 3.0 AUU/AGI.

Above composition is suitable for use in a starch conversion process mentioned below for producing syrup and fermentation products, such as ethanol.

Examples are given below of preferred uses of the polypeptide compositions of the invention. The dosage of the polypeptide composition of the invention and other conditions under which the composition is used may be determined on the basis of methods known in the art.

Uses

The present invention is also directed to processes/methods for using the polypeptides having glucoamylase activity of the invention.

Uses according to the invention include starch conversion of starch to, e.g., syrup and fermentation products, including ethanol and beverages. Examples of processes where a glucoamylase of the invention may be used include the ones described in WO 92/20777, WO 03/066816, WO 03/066826, WO 2004/080923, and WO 2004/081193, which are hereby all incorporated by reference.

Production of Fermentation Products

Process for Producing Fermentation Products from Gelatinized Starch Containing Material In this aspect the present invention relates to a process for producing a fermentation product, especially ethanol, from starch-containing material, which process includes a liquefaction step and sequentially or simultaneously performed saccharification and fermentation steps.

The invention relates to a process for producing a fermentation product from starch-containing material comprising the steps of:

(a) liquefying starch-containing material using an alpha-amylase, (b) saccharifying the liquefied material obtained in step (a) using a glucoamylase of the invention; and (c) fermenting the saccharified material using a fermenting organism.

The fermentation product, such as especially ethanol, may optionally be recovered after fermentation, e.g., by distillation. Suitable starch-containing starting materials are listed in the section "Starch-containing materials"-section below. Contemplated enzymes are listed in the "Enzymes"-section below. The liquefaction is preferably carried out in the presence of an alpha-amylase. The fermentation is preferably carried out in the presence of yeast, preferably a strain of *Saccharomyces*. Suitable fermenting organisms are listed in the "Fermenting Organisms"-section below. In preferred embodiments step (b) and (c) are carried out sequentially or simultaneously (i.e., as SSF process).

In a particular embodiment, the process of the invention further comprises, prior to the step (a), the steps of:

x) reducing the particle size of the starch-containing material, preferably by milling; and (y) forming a slurry comprising the starch-containing material and water.

The aqueous slurry may contain from 10-40 wt. %, preferably 25-35 wt. % starch-containing material. The slurry is heated to above the gelatinization temperature and alpha-amylase, preferably bacterial and/or acid fungal alpha-amylase, may be added to initiate liquefaction (thinning). The slurry may in an embodiment be jet-cooked to further gelatinize the slurry before being subjected to an alpha-amylase in step (a) of the invention.

More specifically liquefaction may be carried out as a three-step hot slurry process. The slurry is heated to between 60-95° C., preferably 80-85° C., and alpha-amylase is added to initiate liquefaction (thinning). Then the slurry may be jet-cooked at a temperature between 95-140° C., preferably 105-125° C., for 1-15 minutes, preferably for 3-10 minute, especially around 5 minutes. The slurry is cooled to 60-95° C. and more alpha-amylase is added to finalize hydrolysis (secondary liquefaction). The liquefaction process is usually carried out at pH 4.5-6.5, in particular at a pH between 5 and 6. Milled and liquefied whole grains are known as mash.

The saccharification in step (b) may be carried out using conditions well know in the art. For instance, a full saccharification process may last up to from about 24 to about 72 hours, however, it is common only to do a pre-saccharification of typically 40-90 minutes at a temperature between 30-65° C., typically about 60° C., followed by complete saccharification during fermentation in a simultaneous saccharification and fermentation process (SSF process). Saccharification is typically carried out at temperatures from 30-65° C., typically around 60° C., and at a pH between 4 and 5, normally at about pH 4.5.

The most widely used process in fermentation product, especially ethanol, production is the simultaneous saccharification and fermentation (SSF) process, in which there is no holding stage for the saccharification, meaning that fermenting organism, such as yeast, and enzyme(s) may be added together. SSF may typically be carried out at a temperature between 25° C. and 40° C., such as between 29° C. and 35° C., such as between 30° C. and 34° C., such as around 32° C. According to the invention the temperature may be adjusted up or down during fermentation.

In accordance with the present invention the fermentation step (c) includes, without limitation, fermentation processes used to produce alcohols (e.g., ethanol, methanol, butanol); organic acids (e.g., citric acid, acetic acid, itaconic acid, lactic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, B12, beta-carotene); and hormones. Preferred fermentation processes include alcohol fermentation processes, as are well known in the art. Preferred fermentation processes are anaerobic fermentation processes, as are well known in the art.

Processes for Producing Fermentation Products from Un-Gelatinized Starch-Containing In this aspect the invention relates to processes for producing a fermentation product from starch-containing material without gelatinization of the starch-containing material (i.e., uncooked starch-containing material). In one embodiment only a glucoamylase of the invention is used during saccharification and fermentation. According to the invention the desired fermentation product, such as ethanol, can be produced without liquefying the aqueous slurry containing the starch-containing material. In one embodiment a process of the invention includes saccharifying (milled) starch-containing material, e.g., granular starch, below the gelatinization temperature in the presence of a glucoamylase of the invention to produce sugars that can be fermented into the desired fermentation product by a suitable fermenting organism.

Accordingly, in this aspect the invention relates to a process for producing a fermentation product from starch-containing material comprising:

(a) saccharifying starch-containing material with a mature glucoamylase according to the invention, preferably having the sequence shown as amino acids 22 to 537 of SEQ ID NO: 2, or amino acids 22 to 651 of SEQ ID NO: 4 or a glucoamylase having at least 75% identity thereto, and preferably also adding an alpha amylase, at a temperature below the initial gelatinization temperature of said starch-containing material, (b) fermenting using a fermenting organism.

Steps (a) and (b) of the process of the invention may be carried out sequentially or simultaneously. In an embodiment a slurry comprising water and starch-containing material is prepared before step (a).

The fermentation process may be carried out for a period of 1 to 250 hours, preferably is from 25 to 190 hours, more preferably from 30 to 180 hours, more preferably from 40 to 170 hours, even more preferably from 50 to 160 hours, yet more preferably from 60 to 150 hours, even yet more preferably from 70 to 140 hours, and most preferably from 80 to 130 hours.

The term "initial gelatinization temperature" means the lowest temperature at which gelatinization of the starch commences. Starch heated in water begins to gelatinize between 50° C. and 75° C.; the exact temperature of gelatinization depends on the specific starch, and can readily be determined by the skilled artisan. Thus, the initial gelatinization temperature may vary according to the plant species, to the particular variety of the plant species as well as with the growth conditions. In the context of this invention the initial gelatinization temperature of a given starch-containing material is the temperature at which birefringence is lost in 5% of the starch granules using the method described by Gorinstein and Lii, 1992, *Starch/Stärke* 44(12): 461-466 (1992).

Before step (a) a slurry of starch-containing material, such as granular starch, having 10-55 wt. % dry solids, preferably 25-40 wt. % dry solids, more preferably 30-35 wt. % dry solids of starch-containing material may be prepared. The slurry may include water and/or process waters, such as stillage (backset), scrubber water, evaporator condensate or distillate, side stripper water from distillation, or other fermentation product plant process water. Because the process of the invention is carried out below the gelatinization temperature and thus no significant viscosity increase takes place, high levels of stillage may be used if desired. In an embodiment the aqueous slurry contains from about 1 to about 70 vol. % stillage, preferably 15-60% vol. % stillage, especially from about 30 to 50 vol. % stillage.

The starch-containing material may be prepared by reducing the particle size, preferably by dry or wet milling, to 0.05 to 3.0 mm, preferably 0.1-0.5 mm. After being subjected to a process of the invention at least 85%, at least 86%, at least 87%, at least 88%, at least 89%, at least 90%, at least 91%, at least 92%, at least 93%, at least 94%, at least 95%, at least 96%, at least 97%, at least 98%, or preferably at least 99% of the dry solids of the starch-containing material is converted into a soluble starch hydrolysate.

The process of the invention is conducted at a temperature below the initial gelatinization temperature. Preferably the temperature at which step (a) is carried out is between 30-75° C., preferably between 45-60° C.

In a preferred embodiment step (a) and step (b) are carried out as a sequential or simultaneous saccharification and fermentation process. In such preferred embodiment the process is typically carried at a temperature between 25° C. and 40° C., such as between 29° C. and 35° C., such as between 30° C. and 34° C., such as around 32° C. According to the invention the temperature may be adjusted up or down during fermentation.

In an embodiment simultaneous saccharification and fermentation is carried out so that the sugar level, such as glucose level, is kept at a low level such as below 6 wt. %, preferably below about 3 wt. %, preferably below about 2 wt. %, more preferred below about 1 wt. %., even more preferred below about 0.5 wt. %, or even more preferred 0.25% wt. %, such as below about 0.1 wt. %. Such low levels of sugar can be accomplished by simply employing adjusted quantities of enzyme and fermenting organism. A skilled person in the art can easily determine which quantities of enzyme and fermenting organism to use. The employed quantities of enzyme and fermenting organism may also be selected to maintain low concentrations of maltose in the fermentation broth. For instance, the maltose level may be kept below about 0.5 wt. % or below about 0.2 wt. %.

The process of the invention may be carried out at a pH in the range between 3 and 7, preferably from pH 3.5 to 6, or more preferably from pH 4 to 5.

Starch-Containing Materials

Any suitable starch-containing starting material, including granular starch, may be used according to the present invention. The starting material is generally selected based on the desired fermentation product. Examples of starch-containing starting materials, suitable for use in a process of present invention, include tubers, roots, stems, whole grains, corns, cobs, wheat, barley, rye, milo, sago, cassava, tapioca, sorghum, rice, peas, beans, or sweet potatoes, or mixtures thereof, or cereals, sugar-containing raw materials, such as molasses, fruit materials, sugar cane or sugar beet, potatoes, and cellulose-containing materials, such as wood or plant residues, or mixtures thereof. Contemplated are both waxy and non-waxy types of corn and barley.

The term "granular starch" means raw uncooked starch, i.e., starch in its natural form found in cereal, tubers or grains. Starch is formed within plant cells as tiny granules insoluble in water. When put in cold water, the starch granules may absorb a small amount of the liquid and swell. At temperatures up to 50° C. to 75° C. the swelling may be reversible. However, with higher temperatures an irreversible swelling called "gelatinization" begins. Granular starch to be processed may be a highly refined starch quality, preferably at least 90%, at least 95%, at least 97% or at least 99.5% pure or it may be a more crude starch containing material comprising milled whole grain including non-starch fractions such as germ residues and fibers. The raw material, such as whole grain, is milled in order to open up the structure and allowing for further processing. Two milling processes are preferred according to the invention: wet and dry milling. In dry milling whole kernels are milled and used. Wet milling gives a good separation of germ and meal (starch granules and protein) and is often applied at locations where the starch hydrolysate is used in production of syrups. Both dry and wet milling is well known in the art of starch processing and is equally contemplated for the process of the invention.

The starch-containing material is reduced in particle size, preferably by dry or wet milling, in order to expose more surface area. In an embodiment the particle size is between 0.05 to 3.0 mm, preferably 0.1-0.5 mm, or so that at least 30%, preferably at least 50%, more preferably at least 70%, even more preferably at least 90% of the starch-containing material fit through a sieve with a 0.05 to 3.0 mm screen, preferably 0.1-0.5 mm screen.

Fermentation Products

The term "fermentation product" means a product produced by a process including a fermentation step using a fermenting organism. Fermentation products contemplated according to the invention include alcohols (e.g., ethanol, methanol, butanol); organic acids (e.g., citric acid, acetic acid, itaconic acid, lactic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, $B_{12}$, beta-carotene); and hormones. In a preferred embodiment the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred beer types comprise ales, stouts, porters, lagers, bitters, malt liquors, happoushu, high-alcohol beer, low-alcohol beer, low-calorie beer or light beer. Preferred fermentation processes used include alcohol fermentation processes, as are well known in the art. Preferred fermentation processes are anaerobic fermentation processes, as are well known in the art.

Fermenting Organisms

"Fermenting organism" refers to any organism, including bacterial and fungal organisms, suitable for use in a fermentation process and capable of producing desired a fermentation product. Especially suitable fermenting organisms are able to ferment, i.e., convert, sugars, such as glucose or maltose, directly or indirectly into the desired fermentation product. Examples of fermenting organisms include fungal organisms, such as yeast. Preferred yeast includes strains of

*Saccharomyces* spp., in particular, *Saccharomyces cerevisiae*. Commercially available yeast include, e.g., Red Star™/Lesaffre Ethanol Red (available from Red Star/Lesaffre, USA) FALI (available from Fleischmann's Yeast, a division of Burns Philp Food Inc., USA), SUPERSTART (available from Alltech), GERT STRAND (available from Gert Strand AB, Sweden) and FERMIOL (available from DSM Specialties).

Enzymes

Glucoamylase

The glucoamylase is preferably a glucoamylase of the invention. However, as mentioned above a glucoamylase of the invention may also be combined with other glucoamylases. The term "glucoamylase" (1,4-alpha-D-glucan glucohydrolase, EC 3.2.1.3) is an enzyme, which catalyzes the release of D-glucose from the non-reducing ends of starch or related oligo- and polysaccharide molecules.

The glucoamylase may added in an amount of 0.001 to 10 AGU/g DS, preferably from 0.01 to 5 AGU/g DS, such as around 0.1, 0.3, 0.5, 1 or 2 AGU/g DS, especially 0.1 to 0.5 AGU/g DS or 0.02-20 AGU/g DS, preferably 0.1-10 AGU/g DS.

Alpha-Amylase

The alpha-amylase may be of any origin. Preferred are alpha-amylases of fungal or bacterial origin.

In a preferred embodiment the alpha-amylase is an acid alpha-amylase, e.g., fungal acid alpha-amylase or bacterial acid alpha-amylase. The term "acid alpha-amylase" means an alpha-amylase (EC 3.2.1.1) which added in an effective amount has activity optimum at a pH in the range of 3 to 7, preferably from 3.5 to 6, or more preferably from 4-5.

Bacterial Alpha-Amylases

A bacterial alpha-amylase may preferably be derived from the genus *Bacillus*.

In a preferred embodiment the *Bacillus* alpha-amylase is derived from a strain of *B. licheniformis, B. amyloliquefaciens, B. subtilis* or *B. stearothermophilus*, but may also be derived from other *Bacillus* sp. Specific examples of contemplated alpha-amylases include the *Bacillus licheniformis* alpha-amylase (BLA) shown in SEQ ID NO: 4 in WO 99/19467, the *Bacillus amyloliquefaciens* alpha-amylase (BAN) shown in SEQ ID NO: 5 in WO 99/19467, and the *Bacillus stearothermophilus* alpha-amylase (BSG) shown in SEQ ID NO: 3 in WO 99/19467. In an embodiment of the invention the alpha-amylase is an enzyme having a degree of identity of at least 60%, preferably at least 70%, more preferred at least 80%, even more preferred at least 90%, such as at least 95%, at least 96%, at least 97%, at least 98% or at least 99% identity to any of the sequences shown as SEQ ID NO: 1, 2, 3, 4, or 5, respectively, in WO 99/19467.

The *Bacillus* alpha-amylase may also be a variant and/or hybrid, especially one described in any of WO 96/23873, WO 96/23874, WO 97/41213, WO 99/19467, WO 00/60059, and WO 02/10355 (all documents hereby incorporated by reference). Specifically contemplated alpha-amylase variants are disclosed in U.S. Pat. Nos. 6,093,562, 6,187,576, and 6,297,038 (hereby incorporated by reference) and include *Bacillus stearothermophilus* alpha-amylase (BSG alpha-amylase) variants having a deletion of one or two amino acid in position 179 to 182, preferably a double deletion disclosed in WO 96/23873—see, e.g., page 20, lines 1-10 (hereby incorporated by reference), preferably corresponding to delta(181-182) compared to the wild-type BSG alpha-amylase amino acid sequence set forth in SEQ ID NO: 3 disclosed in WO 99/19467 or deletion of amino acids 179 and 180 using SEQ ID NO: 3 in WO 99/19467 for numbering (which reference is hereby incorporated by reference). Even more preferred are *Bacillus* alpha-amylases, especially *Bacillus stearothermophilus* alpha-amylase, which have a double deletion corresponding to delta(181-182) and further comprise a N193F substitution (also denoted I181*+G182*+N193F) compared to the wild-type BSG alpha-amylase amino acid sequence set forth in SEQ ID NO: 3 disclosed in WO 99/19467.

The alpha-amylase may also be a maltogenic alpha-amylase. A "maltogenic alpha-amylase" (glucan 1,4-alpha-maltohydrolase, EC 3.2.1.133) is able to hydrolyze amylose and amylopectin to maltose in the alpha-configuration. A maltogenic alpha-amylase from *Bacillus stearothermophilus* strain NCIB 11837 is commercially available from Novozymes A/S, Denmark. The maltogenic alpha-amylase is described in U.S. Pat. Nos. 4,598,048, 4,604,355 and 6,162,628, which are hereby incorporated by reference.

Bacterial Hybrid Alpha-Amylases

A hybrid alpha-amylase specifically contemplated comprises 445 C-terminal amino acid residues of the *Bacillus licheniformis* alpha-amylase (shown as SEQ ID NO: 4 in WO 99/19467) and the 37 N-terminal amino acid residues of the alpha-amylase derived from *Bacillus amyloliquefaciens* (shown as SEQ ID NO: 3 in WO 99/19467), with one or more, especially all, of the following substitutions: G48A+T49I+G107A+H156Y+A181T+N190F+I201F+A209V+Q264S (using the *Bacillus licheniformis* numbering). Also preferred are variants having one or more of the following mutations (or corresponding mutations in other *Bacillus* alpha-amylase backbones): H154Y, A181T, N190F, A209V and Q264S and/or deletion of two residues between positions 176 and 179, preferably deletion of E178 and G179 (using the SEQ ID NO: 5 numbering of WO 99/19467).

The bacterial alpha-amylase may be added in amounts as are well-known in the art. When measured in KNU units (described below in the "Materials & Methods"-section) the alpha-amylase activity is preferably present in an amount of 0.5-5,000 NU/g of DS, in an amount of 1-500 NU/g of DS, or more preferably in an amount of 5-1,000 NU/g of DS, such as 10-100 NU/g DS.

Fungal Alpha-Amylases

Fungal acid alpha-amylases include acid alpha-amylases derived from a strain of the genus *Aspergillus*, such as *Aspergillus kawachii, Aspergillus niger*, or *Aspergillus oryzae* alpha-amylases.

A preferred acid fungal alpha-amylase is a Fungamyl-like alpha-amylase which is preferably derived from a strain of *Aspergillus oryzae*. In the present disclosure, the term "Fungamyl-like alpha-amylase" indicates an alpha-amylase which exhibits a high identity, i.e., more than 70%, more than 75%, more than 80%, more than 85% more than 90%, more than 95%, more than 96%, more than 97%, more than 98%, more than 99% or even 100% identity to the mature part of the amino acid sequence shown in SEQ ID NO: 10 in WO 96/23874.

Another preferred acid alpha-amylase is derived from a strain *Aspergillus niger*. In a preferred embodiment the acid fungal alpha-amylase is the one from *A. niger* disclosed as "AMYA_ASPNG" in the Swiss-prot/TeEMBL database under the primary accession no. P56271 and described in more detail in WO 89/01969 (Example 3). The acid *Aspergillus niger* acid alpha-amylase is also shown as SEQ ID NO: 1 in WO 2004/080923 (Novozymes) which is hereby incorporated by reference. Also variants of said acid fungal amylase having at least 70% identity, such as at least 80% or even at least 90% identity, such as at least 95%, at least 96%, at least 97%, at least 98%, or at least 99% identity to SEQ ID NO: 1 in WO 2004/080923 are contemplated. A suitable commercially available acid fungal alpha-amylase derived from *Aspergillus niger* is SP288 (available from Novozymes A/S, Denmark).

In a preferred embodiment the alpha-amylase is derived from *Aspergillus kawachii* and disclosed by Kaneko et al., 1996, *J. Ferment. Bioeng.* 81: 292-298, "Molecular-cloning and determination of the nucleotide-sequence of a gene encoding an acid-stable alpha-amylase from *Aspergillus kawachii*"; and further as EMBL:#AB008370.

The fungal acid alpha-amylase may also be a wild-type enzyme comprising a carbohydrate-binding module (CBM) and an alpha-amylase catalytic domain (i.e., a none-hybrid), or a variant thereof. In an embodiment the wild-type acid alpha-amylase is derived from a strain of *Aspergillus kawachii*.

Fungal Hybrid Alpha-Amylases

In a preferred embodiment the fungal acid alpha-amylase is a hybrid alpha-amylase. Preferred examples of fungal hybrid alpha-amylases include the ones disclosed in WO 2005/003311 or U.S. Application Publication no. 2005/0054071 (Novozymes) or U.S. application No. 60/638,614 (Novozymes) which is hereby incorporated by reference. A hybrid alpha-amylase may comprise an alpha-amylase catalytic domain (CD) and a carbohydrate-binding domain/module (CBM) and optional a linker.

Specific examples of contemplated hybrid alpha-amylases include those disclosed in U.S. application No. 60/638,614 including Fungamyl variant with catalytic domain JA118 and *Athelia rolfsii* SBD (SEQ ID NO: 100 in U.S. application No. 60/638,614), *Rhizomucor pusillus* alpha-amylase with *Athelia rolfsii* AMG linker and SBD (SEQ ID NO: 101 in U.S. application No. 60/638,614) and *Meripilus giganteus* alpha-amylase with *Athelia rolfsii* glucoamylase linker and SBD (SEQ ID NO: 102 in U.S. application No. 60/638,614).

Other specific examples of contemplated hybrid alpha-amylases include those disclosed in U.S. Application Publication no. 2005/0054071, including those disclosed in Table 3 on page 15, such as *Aspergillus niger* alpha-amylase with *Aspergillus kawachii* linker and starch binding domain.

Commercial Alpha-Amylase Products

Preferred commercial compositions comprising alpha-amylase include MYCOLASE from DSM (Gist Brocades), BAN™, TERMAMYL™ SC, FUNGAMYL™, LIQUOZYME™ X and SAN™ SUPER, SAN™ EXTRA L (Novozymes A/S) and CLARASE™ L-40,000, DEX-LO™, SPEZYME™ FRED, SPEZYME™ AA, SPEZYME™ Ethyl, GC358, GC980, SPEZYME™ RSL, and SPEZYME™ DELTA AA (Genencor Int.), and the acid fungal alpha-amylase sold under the trade name SP288 (available from Novozymes A/S, Denmark).

An acid alpha-amylase may according to the invention be added in an amount of 0.1 to 10 AFAU/g DS, preferably 0.10 to 5 AFAU/g DS, especially 0.3 to 2 AFAU/g DS.

Production of Syrup

The present invention also provides a process of using a glucoamylase of the invention for producing syrup, such as glucose and the like, from starch-containing material. Suitable starting materials are exemplified in the "Starch-containing materials"-section above. Generally, the process comprises the steps of partially hydrolyzing starch-containing material (liquefaction) in the presence of alpha-amylase and then further saccharifying the release of glucose from the non-reducing ends of the starch or related oligo- and polysaccharide molecules in the presence of glucoamylase of the invention.

Liquefaction and saccharification may be carried our as described above for fermentation product production.

The glucoamylase of the invention may also be used in immobilized form. This is suitable and often used for producing specialty syrups, such as maltose syrups, and further for the raffinate stream of oligosaccharides in connection with the production of fructose syrups, e.g., high fructose syrup (HFS).

Consequently, this aspect of the invention relates to a process of producing syrup from starch-containing material, comprising (a) liquefying starch-containing material in the presence of an alpha-amylase, and (b) saccharifying the material obtained in step (a) using a glucoamylase of the invention.

A syrup may be recovered from the saccharified material obtained in step (b).

Details on suitable conditions can be found above.

Brewing

A glucoamylase of the invention can also be used in a brewing process. The glucoamylase of the invention is added in effective amounts which can be easily determined by the skilled person in the art.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties. The present invention is further described by the following examples which should not be construed as limiting the scope of the invention.

Signal Peptide and Propeptide

The present invention also relates to an isolated polynucleotide encoding a signal peptide comprising or consisting of amino acids 1 to 21 of SEQ ID NO: 2 or of SEQ ID NO: 4. The polynucleotides may further comprise a gene encoding a protein, which is operably linked to the signal peptide. The protein is preferably foreign to the signal peptide and/or propeptide. In one aspect, the polynucleotide encoding the signal peptide is nucleotides 1 to 63 of SEQ ID NO: 1 or of SEQ ID NO: 3.

The present invention also relates to nucleic acid constructs, expression vectors and recombinant host cells comprising such polynucleotides.

The present invention also relates to methods of producing a protein, comprising (a) cultivating a recombinant host cell comprising such polynucleotide; and (b) recovering the protein.

The protein may be native or heterologous to a host cell. The term "protein" is not meant herein to refer to a specific length of the encoded product and, therefore, encompasses peptides, oligopeptides, and polypeptides. The term "protein" also encompasses two or more polypeptides combined to form the encoded product. The proteins also include hybrid polypeptides and fused polypeptides.

Preferably, the protein is a hormone, enzyme, receptor or portion thereof, antibody or portion thereof, or reporter. For example, the protein may be a hydrolase, isomerase, ligase, lyase, oxidoreductase, or transferase, e.g., an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase, xylanase, or beta-xylosidase.

The gene may be obtained from any prokaryotic, eukaryotic, or other source.

The present invention is further described by the following examples that should not be construed as limiting the scope of the invention.

EXAMPLES

Glucoamylase Activity

Glucoamylase activity may be measured in AGI units or in Glucoamylase Units (AGU), or according to other suitable assays like e.g. a commercial assay kit from Kikkoman or Wako (LabAssay glucose, WAKO, Cat#298-65701).
Glucoamylase Activity (AGI)

Glucoamylase (equivalent to amyloglucosidase) converts starch into glucose. The amount of glucose is determined here by the glucose oxidase method for the activity determination. The method described in the section 76-11 Starch—Glucoamylase Method with Subsequent Measurement of Glucose with Glucose Oxidase in "Approved methods of the American Association of Cereal Chemists". Vol. 1-2 AACC, from American Association of Cereal Chemists, (2000); ISBN: 1-891127-12-8.

One glucoamylase unit (AGI) is the quantity of enzyme which will form 1 micro mole of glucose per minute under the standard conditions of the method.
Standard Conditions/Reaction Conditions:
  Substrate: Soluble starch, concentration approx. 16 g dry matter/L.
  Buffer: Acetate, approx. 0.04 M, pH=4.3
  pH: 4.3
  Incubation temperature: 60° C.
  Reaction time: 15 minutes
  Termination of the reaction: NaOH to a concentration of approximately 0.2 g/L (pH~9)
  Enzyme concentration: 0.15-0.55 AAU/mL.

The starch should be Lintner starch, which is a thin-boiling starch used in the laboratory as colorimetric indicator. Lintner starch is obtained by dilute hydrochloric acid treatment of native starch so that it retains the ability to color blue with iodine.
Glucoamylase Activity (AGU)

The Novo Glucoamylase Unit (AGU) is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

| AMG incubation: | |
|---|---|
| Substrate: | maltose 23.2 mM |
| Buffer: | acetate 0.1M |
| pH: | 4.30 ± 0.05 |
| Incubation temperature: | 37° C. ± 1 |
| Reaction time: | 5 minutes |
| Enzyme working range: | 0.5-4.0 AGU/mL |

| Color reaction: | |
|---|---|
| GlucDH: | 430 U/L |
| Mutarotase: | 9 U/L |
| NAD: | 0.21 mM |
| Buffer: | phosphate 0.12M; 0.15M NaCl |
| pH: | 7.60 ± 0.05 |
| Incubation temperature: | 37° C. ± 1 |
| Reaction time: | 5 minutes |
| Wavelength: | 340 nm |

Glucoamylase Activity Assay (Kikkoman)
Product code: 60211
This kit is for measurement of the glucose-forming activity in rice koji.
Assay Principle:

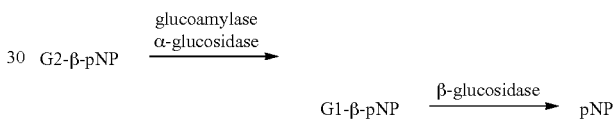

The substrate, 4-nitrophenyl-β-maltoside (G2-3-pNP) is degraded by glucoamylase or α-glucosidase into 4-nitrophenyl-β-glucoside (G1-β-pNP). G1-β-pNP is further degraded into 4-nitrophenol (pNP) by β-glucosidase in this kit. Reaction is performed at room temperature at pH about 4. The reaction is stopped by addition of sodium carbonate, and at the same time the solution becomes alkaline pH to maximize the absorbance of pNP. The glucose-forming activity is measured by quantifying the pNP at 400 nm.
1) The measured response shows the G2-β-pNP degradation activity of glucoamylase and α-glucosidase in the sample. This is thought to be the glucose forming activity in the sample.
2) The test can be used for rice koji extract without dialysis.
3) This assay is not affected by α-amylase in the sample.

| Kit components | | |
|---|---|---|
| Reagent | Main component | Amount |
| substrate solution | G2-β-pNP | 60 ml |
| enzyme solution | β-glucosidase | 60 ml |
| stop solution | sodium carbonate | 120 ml |

1) Mix "substrate solution" and "enzyme solution" of the kit at 1:1.
2) Pipette 20 µl of the sample (or water as a blank) and transfer it to a microtiter plate well. (duplicate)
3) Add 60 µl of the substrate-enzyme mixture to the well.
4) Incubate at room temperature for 20 min.
5) Add 120 µl of the stop solution to the well.
6) Read OD400 nm. # Net $OD_{400}=OD_{400}$(sample)–$OD_{400}$ (blank)

1. Blank: Usually, the blank absorbance is less than 0.200.
2. Specificity: The response is not affected by glucose (up to 100 g/l) or α-amylase (725 U/ml).
3. Reproducibility: The CV of absorbance is less than 1% when the same sample is analyzed 10 times.
4. Linear range: The net $OD_{400}$ up to 1.6 should be proportional to the enzyme concentration.
5. Stability of color: The absorbance does not change for 2 h at 25° C.

Wako Glucose Assay Kit (LabAssay Glucose, WAKO, Cat#298-65701).

LabAssay™ Glucose is a reagent kit for assay of glucose based on an enzymatic method with a combination of mutarotase and glucose oxidase.

α-D-glucose and β-D-glucose in solution maintain equilibrium in a constant ratio. Glucose oxidase reacts only with β-D-glucose and does not react with α-D-glucose. Therefore, α-D-glucose is converted into β-D-glucose using mutarotase.

When a sample is mixed with the Chromogen Reagent, the alpha-form of glucose in the sample is converted to beta-form by mutarotase. Beta-D-glucose is oxidized and yields hydrogen peroxide by glucose oxidase (GOD). In the presence of peroxidase (POD), the formed hydrogen peroxide yields a red pigment by quantitative oxidation condensation with phenol and 4-aminoantipyrine. The glucose concentration is obtained by measuring absorbance of the red pigment. The assay was performed in 96 wells microplates using a microplate reader with 505 nm wavelength filter. Assay was performed at 37° C. for 5 min.

The principle of the assay method is further described in Miwa, et al., 1972, Clin. Chim. Acta., 37, 538-540.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Materials

Chemicals used as buffers and substrates were commercial products of at least reagent grade.

Strains

*Penicillium emersonii* (NN051602) was used as the source of polypeptides having glucoamylse activity. NN051602 was isolated from compost from Yunnan province China, 2009. Sequence information suggest that this isolate is very closely related to *Talaromyces emersonii* and may in fact be the same species or its anamorph. In the examples the strain is therefore referred to as *Talaromyces emersonii*. *Aspergillus niger* strain HowB112 was used for expression of the *T. emersonii* genes encoding the polypeptides having glucoamylse activity. *A. niger* HowB112 is an amdS (acetamidase) gene disrupted derivative of *A. niger* BO1. Strain HowB112 bears following genotypes: AMG⁻ (disrupted glucoamylase gene), ASA⁻ (disrupted acid stable amylase gene) and tgs⁻ (disrupted alpha-1,6-transglucosidase gene).

Media and Solutions

YMD medium was composed of 0.3% yeast extract, 0.5% peptone, of 0.3% malt extract and 5% maltodextrin.

PDA agar plates were composed of potato infusion (potato infusion was made by boiling 300 g of sliced (washed but unpeeled) potatoes in water for 30 minutes and then decanting or straining the broth through cheesecloth. Distilled water was then added until the total volume of the suspension was one liter, followed by 20 g of dextrose and 20 g of agar powder. The medium was sterilized by autoclaving at 15 psi for 15 minutes (Bacteriological Analytical Manual, 8th Edition, Revision A, 1998).

LB plates were composed of 10 g of Bacto-Tryptone, 5 g of yeast extract, 10 g of sodium chloride, 15 g of Bacto-agar, and deionized water to 1 liter.

LB medium was composed of 10 g of Bacto-Tryptone, 5 g of yeast extract, and 10 g of sodium chloride, and deionized water to 1 liter.

YPG medium contained 0.4% of yeast extract, 0.1% of KH2PO4, 0.05% of MgSO4.7H2O, 1.5% glucose in deionized water COVE-N-gly slants were composed of 218 g sorbitol, 10 g glycerol, 2.02 g KNO3, 50 ml COVE salt solution, 25 g agar powder and deionized water to 1 liter.

COVE plates for protoplast regeneration were composed of 342 g of sucrose, 20 g of agar powder, 20 ml of COVE salt solution, and deionized water to 1 liter. The medium was sterilized by autoclaving at 15 psi for 15 minutes (Bacteriological Analytical Manual, 8th Edition, Revision A, 1998). The medium was cooled to 60° C. and 10 mM acetamide, 15 mM CsCl, were added.

COVE top agarose were composed of 342.3 g sucrose, 20 ml COVE salt solution, 6 g GTG agarose (SeaKem, Cat#50070) and deionized water to 1 liter. The medium was sterilized by autoclaving at 15 psi for 15 minutes (Bacteriological Analytical Manual, 8th Edition, Revision A, 1998). The medium was cooled to 60° C., and 10 mM acetamide and 15 mM CsCl were added.

COVE-2 plate for isolation were composed of 30 g sucrose, 20 ml COVE salt solution, 30 g agar powder and deionized water to 1 liter. The medium was sterilized by autoclaving at 15 psi for 15 minutes (Bacteriological Analytical Manual, 8th Edition, Revision A, 1998). The medium was cooled to 60° C. and 10 mM acetamide was added.

COVE salt solution was composed of 26 g of $MgSO_4.7H_2O$, 26 g of KCL, 26 g of $KH_2PO_4$, 50 ml of COVE trace metal solution, and deionized water to 1 liter.

COVE trace metal solution was composed of 0.04 g of Na2B4O7.10H2O, 0.4 g of $CuSO_4.5H_2O$, 1.2 g of $FeSO_4.7H_2O$, 0.7 g of $MnSO_4.H_2O$, 0.8 g of $Na_2MoO_4.2H_2O$, 10 g of $ZnSO_4.7H_2O$, and deionized water to 1 liter.

MD medium was composed of 1.34% YNB, $4\times10^{-5}$% biotin and 2% dextrose. For plates, 7.5 g agar was added to 200 ml of water autoclave, cooled to 60° C. and then 25 ml of 10×YNB, 25 ml of 10×D-glucose and 400 μl of 500× biotin were added.

BMSY was composed of 1% yeast extract, 2% peptone (Bacto), 100 mM potassium phosphate buffer, pH 6.0, 1.34% YNB, $4\times10^{-5}$% biotin and 1.82% Sorbitol.

10 g of yeast extract, 20 g peptone (Bacto) and 18.2 g Sorbitol were dissolved in 800 ml water and autoclaved for 20 minutes on liquid cycle. When the autoclaved medium was cooled to room temperature, 100 ml of 1 M potassium phosphate buffer (pH 6.0) and 100 ml of 10×YNB and 2 ml of 500× biotin were added.

Example 1

*Talaromyces Emersonii* Genomic DNA Extraction

*Talaromyces emersonii* strain NN051602 was inoculated onto a PDA plate and incubated for 3 days at 45° C. in the darkness. Several mycelia-PDA plugs were inoculated into 500 ml shake flasks containing 100 ml of YPG medium. The flasks were incubated for 3 days at 45° C. with shaking at 160 rpm. The mycelia were collected by filtration through MIRACLOTH® (Calbiochem, La Jolla, Calif., USA) and frozen in liquid nitrogen. Frozen mycelia were ground, by a mortar and a pestle, to a fine powder, and genomic DNA was isolated using DNeasy® Plant Maxi Kit (QIAGEN Inc., Valencia, Calif., USA) following the manufacturer's instruction.

Example 2

Cloning of 2 GH15 Glucoamylase Genes from the *Talaromyces Emersonii* Genomic DNA Oligonucleotide primers, shown below in table 2, were designed to amplify the GH15 glucoamylse genes (SEQ ID: 1 and 3) from the genomic DNA of *Talaromyces emersonii* NN051602. Primers were synthesized by Invitrogen (Invitrogen, Beijing, China).

TABLE 1

GH15 glucoamylse genes from *Talaromyces ermersonii*

| Gene name | DNA sequence |
|---|---|
| AMG51602-1 | SEQ ID: 1 |
| AMG51602-2 | SEQ ID: 3 |

TABLE 2

Primers to amplify full-length glucoamylse genes from *Talaromyces emersonii* genomic DNA

| Related SEQ ID | Primer name | Sequence (5'-3') |
|---|---|---|
| 1_forward SEQ ID NO: 5 | AMG51602-1_C505_bam | acacaactggggatccaccc ATGTTGGTCAAGTCCTTGTTGTCTC |
| 1_reverse SEQ ID NO: 6 | AMG51602-1_C505_xho | ccctctagatctcgagcta TGCTCCTGCTGCGCCAGGGCTACC |
| 2_forward SEQ ID NO: 7 | AMG51602-2_C505_bam | acacaactggggatccacc ATGGCTTCTCCTCTGTCTTATGCG |
| 2_reverse SEQ ID NO: 8 | AMG51602-2_C505_xho | ccctctagatctcgag TTTCACCGCCACGTATCGCT |

Upper characters represent the 5'- and 3'-regions of the genes to be amplified, while lower cases were homologous to the vector sequences at insertion sites of pCaHj505 vector. The expression vector pCaHj505 contained the TAKA-amylase promoter derived from *Aspergillus oryzae* and the *Aspergillus niger* glucoamylase terminator elements. Furthermore pCaHj505 had pUC18 derived sequences for selection and propagation in *E. coli*, and an amdS gene, which encoded an acetoamidase gene derived from *Aspergillus nidulans* for selection of an amdS+ *Aspergillus* transformant.

For each gene, 20 pmol of primer pair (each of the forward and reverse) were used in a PCR reaction composed of 2 µl of *Talaromyces emersonni* NN051602 genomic DNA, 10 µl of 5×GC Buffer, 1.5 µl of DMSO, 2.5 mM each of dATP, dTTP, dGTP, and dCTP, and 0.6 unit of Phusion™ High-Fidelity DNA Polymerase (Finnzymes Oy, Espoo, Finland) in a final volume of 50 µl. The amplification was performed using a Peltier Thermal Cycler (M J Research Inc., South San Francisco, Calif., USA) programmed for denaturing at 98° C. for 1 minutes; 10 cycles of denaturing at 98° C. for 15 seconds, annealing at 65° C. for 30 seconds, with 1° C. decrease per cycle and elongation at 72° C. for 90 seconds; and another 26 cycles each at 98° C. for 15 seconds, 60° C. for 30 seconds and 72° C. for 90 seconds; final extension at 72° C. for 10 minutes. The heat block then went to a 4° C. soak cycle.

The PCR products were isolated by 0.7% agarose gel electrophoresis using 90 mM Tris-borate and 1 mM EDTA (TBE) buffer where product bands at expected size of each PCR reaction were visualized under UV light. The PCR products were then purified from solution by using a GFX PCR DNA and Gel Band Purification Kit (GE Healthcare, Buckinghamshire, UK) according to the manufacturer's instructions.

TABLE 3

Size of PCR products in Example 2

| Gene name | Size of PCR product |
|---|---|
| AMG51602-1 | 1.9 kb |
| AMG51602-2 | 2.3 kb |

Plasmid pCaHj505 was digested with BamHI and XhoI, isolated by 0.7% agarose gel electrophoresis using TBE buffer, and purified using an illustra PCR DNA and Gel Band Purification Kit according to the manufacturer's instructions.

An In-Fusion CF Dry-down Cloning Kit (Clontech Laboratories, Inc., Mountain View, Calif., USA) was used to clone the fragment directly into the expression vector pCaHj505.

The PCR products and the digested vector were ligated together using an IN-FUSION™ CF Dry-down Cloning Kit (Clontech Laboratories, Inc., Mountain View, Calif., USA) resulting in plasmids in Table 4 respectively, in which transcription of *Humicola insolens* GH15 glucoamylse genes was under the control of a TAKA-amylase promoter from *Aspergillus oryzae*. The cloning operation was according to the manufacturer's instruction. In brief, for each ligation reaction 30 ng of with BamHI and XhoI digested pCaHj505 and 60 ng of purified PCR products were added to the reaction vial and resuspended with the powder in a final volume of 10 µl with addition of deionized water. The reactions were incubated at 37° C. for 15 minutes and then 50° C. for 15 minutes. 3 µl of the reaction were transformed into *E. coli* TOP10 competent cells (TIANGEN Biotech (Beijing) Co. Ltd., Beijing, China) according to the manufacturer's protocol and plated onto LB plates supplemented with 0.1 mg of ampicillin per ml. After incubating at 37° C. overnight, colonies were seen growing on the LB ampicillin plates. *E. coli* transformants containing expression constructs were detected by colony PCR and confirmed by DNA sequencing with vector primers (by SinoGenoMax Company Limited, Beijing, China). Plasmid DNA pAMG51602-1_C505 and pAMG51602-2_C505 for expression in *A. niger* were extracted from correct *E. coli* transformants, by using a QIAprep Spin Miniprep Kit (QIAGEN Inc., Valencia, Calif., USA).

TABLE 4

Plasmid (Expression constructs) in Example 2

| Gene name | Plasmid |
|---|---|
| AMG51602-1 | pAMG51602-1_C505 |
| AMG51602-2 | pAMG51602-2_C505 |

Example 3

Expression of *Talaromyces Emersonii* GH15 Glucoamylase Genes in *Aspergillus niger*

An agar slant (COVE-N-gly) was inoculated with spores of *Aspergillus niger* HowB112, and grown at 32° C. until it was completely sporulated. The spores were resuspended in 5-10 ml of sterile 0.05% tween20 water. About $10^8$ spores were transferred to a 500 ml baffled shake flask containing 100 ml YPG medium with 10 mM $NaNO_3$, and incubated at 32° C. for 16 hrs at 99 rpm in Innova shaker. Then the mycelia were harvested for protoplasts preparation. *Aspergillus niger* HowB112 protoplasts preparation and transformation were done according to the method described in patent WO 2004/111218 or EP 238023. 10 μg of pAMG51602-1_C505 and pAMG51602-2_C505 each were used to transform *Aspergillus niger* HowB112 separately.

The *Aspergillus niger* HowB112 transformants with pAMG51602-1_C505 and pAMG51602-2_C505 were selected on the COVE plates for protoplast regeneration (described in the Media and Solution part). About 15 transformants were observed on the selective plates for each transformation. Six transformants from each transformation were isolated on COVE-2 plate for 3-4 days at 32° C. After isolation those six transformants for each transformation were inoculated separately into 3 ml of YMD medium in 24-well plate and incubated at 30° C., 220 rpm. After 3 days incubation, 20 μl of supernatant from each culture were analyzed on NuPAGE Novex 4-12% Bis-Tris Gel w/MES (Invitrogen Corporation, Carlsbad, Calif., USA) according to the manufacturer's instructions. The resulting gel was stained with Instant Blue (Expedeon Ltd., Babraham Cambridge, UK). SDS-PAGE profiles of the cultures showed that they had the excepted protein bands of expression products of pAMG51602-1_C505 and pAMG51602-2_C505. The expression product numbers and expression strain numbers of those six genes were shown in Table 5.

TABLE 5

| | Expression strains | |
|---|---|---|
| Expression construct | Expression product | Expression strain |
| pAMG51602-1_C505 | P245A6 | O5MXC |
| pAMG51602-2_C505 | P245A5 | O5MXB |

Example 4

Fermentation of *A. niger* Expression Strains

A slant of each expression strain in Table 5 was washed with 10 ml of YMD and inoculated into a 2 liter flask containing 400 ml of YMD medium to generate broth for characterization of the enzyme. The culture was incubated at 30° C. on shaker at 150 rpm. The culture was harvested on day 3 and filtered using a 0.45 μm DURAPORE Membrane (Millipore, Bedford, Mass., USA). The filtered culture broth was used for enzyme characterization.

Example 5

Characterization of Glucoamylases

Substrate: 1% soluble starch (Sigma S-9765) in deionized water
Reaction buffer: 0.1 M Acetate buffer at pH4.3
Glucose concentration determination kit: Wako glucose assay kit (LabAssay glucose, WAKO, Cat#298-65701).

Reaction Condition:
20 μl soluble starch and 50 μl acetate buffer at pH5.3 were mixed. 30 μl enzyme solution (50 μg enzyme protein/ml) was added to a final volume of 100 μl followed by incubation at 37° C. for 15 min.

The glucose concentration is determined by Wako kits.
All the experiments were carried out in parallel.

Temperature Optimum.
To assess the temperature profile, the Reaction condition assay described above was performed at 20, 30, 40, 50, 60, 70, 80, and 90° C. The results are shown in table 6.

TABLE 6

| | | Temperature optimum | | | | | | | |
|---|---|---|---|---|---|---|---|---|---|
| Temperature (° C.) | | 20 | 30 | 40 | 50 | 60 | 70 | 80 | 90 |
| Relative activity (%) | P245A6 | 54.8 | 65.7 | 87.7 | 91.9 | 100.0 | 94.4 | 72.6 | 57.9 |
| | P245A5 | 58.0 | 66.7 | 81.1 | 96.5 | 100.0 | 85.3 | 63.8 | 49.6 |

From the result it can be seen that the optimal temperature for P245A6 and P245A5 at the given conditions is around 60° C. and the glucoamylase maintains near 50% activity at 90° C.

Heat Stability:
To assess the heat stability of these glucoamylases the Reaction condition assay was modified in that the enzyme solution and acetate buffer was preincubated at 60° C. for 0, 10, 30, 60, and 120 minutes. Following the incubation 20 μl of starch was added to the solution and the assay was performed as described above.

The results were shown in table 7.

TABLE 7

| | | Heat stability | | | | |
|---|---|---|---|---|---|---|
| Incubation time (min) | | 0 | 10 | 30 | 60 | 120 |
| Relative activity (%) | P245A6 (60° C.) | 100.0 | 81.2 | 72.1 | 33.7 | 32.8 |
| | P245A5 (60° C.) | 100.0 | 93.9 | 72.6 | 67.6 | 66.1 | pH Optimum:
To assess the pH optimum of the glucoamylases the Reaction condition assay described above was performed at pH 2.0, 3.0, 4.0, 5.0, 6.0 7.0, 8.0, 9.0, 10.0 and 11.0. Instead of using the acetate buffer described in the Reaction condition assay the following buffer was used 100 mM Succinic acid, HEPES, CHES, CAPSO, 1 mM $CaCl_2$, 150 mM KCl, 0.01% Triton X-100, pH adjusted to 2.0, 3.0, 3.5, 4.0, 4.5, 5.0, 6.0 7.0, 8.0, 9.0, 10.0 or 11.0 with HCl or NaOH.

The results were shown in table 8.

TABLE 8

| | pH | 2.0 | 3.0 | 4.0 | 5.0 | 6.0 | 7.0 | 8.0 | 9.0 | 10.0 | 11.0 |
|---|---|---|---|---|---|---|---|---|---|---|---|
| Relative activity (%) | P245A6 | 60.1 | 77.1 | 100.0 | 96.7 | 45.4 | 33.6 | 31.1 | 33.7 | 31.9 | 25.6 |
| | P245A5 | 56.7 | 55.7 | 89.2 | 100.0 | 92.7 | 68.8 | 55.2 | 57.6 | 56.6 | 57.0 |

From the result it can be seen that P245A6 and P245A5 are acidic enzymes having an optimal pH at 4 and 5 respectively.

pH Stability:

30 µl enzyme solution (50 µg/ml) and 50 µl buffer at was mixed and preincubated for 0, 10, 30, 60, 120 mins. After preincubation, 20 µl soluble starch in a final volume of 100 µl was incubated at 37° C. for 15 min.
Finally the glucose concentration was determined using the Wako kits. The results are shown in table 9.

TABLE 9

| | pH stability | | | | | |
|---|---|---|---|---|---|---|
| Incubation time (min) | | 0 | 10 | 30 | 60 | 120 |
| Relative activity (%) | P245A6 (pH 4) | 100.0 | 91.2 | 91.7 | 143.8 | 211.6 |

TABLE 9-continued

| | pH stability | | | | | |
|---|---|---|---|---|---|---|
| Incubation time (min) | | 0 | 10 | 30 | 60 | 120 |
| (%) | P245A5 (pH 5) | 100.0 | 113.9 | 98.3 | 95.5 | 104.2 |

From the result it can be seen that the two glucoamylases are stable at acidic condition under the conditions tested.

The invention claimed is:

1. A composition comprising a polypeptide having at least 95% sequence identity to the mature polypeptide of SEQ ID NO: 2 or SEQ ID NO: 4, wherein the polypeptide has glucoamylase activity.

2. A composition comprising an alpha-amylase and a polypeptide having at least 95% sequence identity to the mature polypeptide of SEQ ID NO: 2 or SEQ ID NO: 4, wherein the polypeptide has glucoamylase activity.

3. A process of producing a fermentation product from starch-containing material comprising the steps of:
   (a) liquefying starch-containing material;
   (b) saccharifying the liquefied material to form a saccharified material; and
   (c) fermenting the saccharified material with a fermenting organism;
wherein step (b) is carried out using at least a glucoamylase having at least at least 95% sequence identity to the mature polypeptide of SEQ ID NO: 2 or SEQ ID NO: 4.

4. A process of producing a fermentation product from starch-containing material, comprising the steps of:
   (a) saccharifying starch-containing material with an alpha amylase and a glucoamylase having at least at least 95% sequence identity to the mature polypeptide of SEQ ID NO: 2 or SEQ ID NO: 4, at a temperature below the initial gelatinization temperature of said starch-containing material to form saccharified material; and
   (b) fermenting the saccharified material with a fermenting organism.

5. A recombinant nucleic acid construct or recombinant expression vector comprising a polynucleotide encoding a polypeptide having at least 95% sequence identity to the mature polypeptide of SEQ ID NO: 2 or SEQ ID NO: 4 operably linked to one or more control sequences that direct the production of the polypeptide in an expression host.

6. A recombinant host cell comprising a polynucleotide encoding a polypeptide having at least 95% sequence identity to the mature polypeptide of SEQ ID NO: 2 or SEQ ID NO: 4 operably linked to one or more control sequences that direct the production of the polypeptide.

7. A method of producing a polypeptide of having at least at least 95% sequence identity to the mature polypeptide of SEQ ID NO: 2 or SEQ ID NO: 4, comprising:
   (a) cultivating a recombinant host cell comprising a polynucleotide encoding a polypeptide having at least 95% sequence identity to the mature polypeptide of SEQ ID NO: 2 or SEQ ID NO: 4 under conditions conducive for production of the polypeptide; and
   (b) recovering the polypeptide.

8. A transgenic plant, plant part or plant cell transformed with a polynucleotide encoding a polypeptide having at least at least 95% sequence identity to the mature polypeptide of SEQ ID NO: 2 or SEQ ID NO: 4.

9. A method of producing a polypeptide having at least at least 95% sequence identity to the mature polypeptide of SEQ ID NO: 2 or SEQ ID NO: 4, comprising:
   (a) cultivating the transgenic plant or plant cell of claim 8 under conditions conducive for production of the polypeptide; and
   (b) recovering the polypeptide.

10. The recombinant host cell of claim 6, wherein the host cell is *Candida, Hansenula, Kluyveromyces, Pichia, Saccharomyces, Schizosaccharomyces*, or *Yarrowia*.

11. The recombinant host cell of claim 10, wherein the host cell is *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis*.

12. The recombinant host cell of claim 10, wherein the host cell is *Saccharomyces cerevisiae*.

13. A method of producing a polypeptide of having at least at least 95% sequence identity to the mature polypeptide of SEQ ID NO: 2 or SEQ ID NO: 4, comprising:
   (a) cultivating a recombinant host cell comprising a polynucleotide encoding a polypeptide having at least at least 95% sequence identity to the mature polypeptide of SEQ ID NO: 2 or SEQ ID NO: 4 under conditions conducive for production of the polypeptide; and
   (b) recovering the polypeptide, wherein the polypeptide has glucoamylase activity.

14. The method of claim 13, wherein the polypeptide has at least 96% sequence identity to the mature polypeptide of SEQ ID NO: 2 or SEQ ID NO: 4.

15. The method of claim 13, wherein the polypeptide has at least 97% sequence identity to the mature polypeptide of SEQ ID NO: 2 or SEQ ID NO: 4.

16. The method of claim 13, wherein the polypeptide has at least 98% sequence identity to the mature polypeptide of SEQ ID NO: 2 or SEQ ID NO: 4.

17. The method of claim 13, wherein the polypeptide has at least 99% sequence identity to the mature polypeptide of SEQ ID NO: 2 or SEQ ID NO: 4.

18. The recombinant host cell of claim 6, wherein the polynucleotide encodes a polypeptide having at least at least 99% sequence identity to the mature polypeptide of SEQ ID NO: 2 or SEQ ID NO: 4.

* * * * *